US012577570B2

(12) United States Patent
Itoh et al.

(10) Patent No.: US 12,577,570 B2
(45) Date of Patent: Mar. 17, 2026

(54) MODIFIED NEURAMINIDASE

(71) Applicant: Tokushima University, Tokushima (JP)

(72) Inventors: Kohji Itoh, Tokushima (JP); Jun Tsukimoto, Tokushima (JP)

(73) Assignee: Tokushima University, Tokushima (JP)

( * ) Notice: Subject to any disclaimer, the term of this patent is extended or adjusted under 35 U.S.C. 154(b) by 1109 days.

(21) Appl. No.: 17/623,302

(22) PCT Filed: Jul. 3, 2020

(86) PCT No.: PCT/JP2020/026174

§ 371 (c)(1),
(2) Date: Dec. 28, 2021

(87) PCT Pub. No.: WO2021/006202

PCT Pub. Date: Jan. 14, 2021

(65) Prior Publication Data

US 2022/0364101 A1 Nov. 17, 2022

(30) Foreign Application Priority Data

Jul. 5, 2019 (JP) ................................ 2019-126376

(51) Int. Cl.

| | |
|---|---|
| *C12N 15/52* | (2006.01) |
| *A61P 3/00* | (2006.01) |
| *C12N 9/48* | (2006.01) |
| *C12N 15/86* | (2006.01) |

(52) U.S. Cl.

CPC ............... *C12N 15/52* (2013.01); *A61P 3/00* (2018.01); *C12N 9/485* (2013.01); *C12N 15/86* (2013.01); *C12N 2750/14143* (2013.01)

(58) Field of Classification Search

CPC ........ C12N 15/52; C12N 9/485; C12N 15/86; C12N 2750/14143; C12N 9/2402; C12N 2800/107; A61P 3/00; A61P 43/00; A01K 2217/075; A01K 2227/105; A01K 2267/0306; A61K 38/00; A61K 38/47; A61K 48/0008; A61K 48/005; C12Y 302/01018; C12Y 304/16005

See application file for complete search history.

(56) References Cited

FOREIGN PATENT DOCUMENTS

| | | |
|---|---|---|
| JP | 2014526904 A | 10/2014 |
| WO | WO-9831817 A2 * | 7/1998 ........... C12N 9/2402 |
| WO | 2013/033074 A2 | 3/2013 |
| WO | 2016/167392 A1 | 10/2016 |

OTHER PUBLICATIONS

Tsukimoto et al. (2018) "Suppression of Intracellular Crystallization of Human Neuraminidase 1 NEU1 by Amino Acid Substitution and its Medical Application", Abstracts of the 41st Annual Conference of the Molecular Biology Society of Japan [3P-0079], English Abstract Only.

Tsukimoto et al. (Nov. 19, 2019) "Control of Intracellular Crystallization of Human Neuraminidase 1 and its Therapeutic Application", Abstracts of the 42nd annual conference of the Molecular Biology Society of Japan [1P-0039], English Abstract Only.

Tsukimoto et al. (Sep. 4, 2019) "Suppression of Intracellular Crystallization of Human Neuraminidase 1 and its Application to the Treatment of Lysosomal Storage Diseases", Abstracts of the 92nd annual meeting of the Japanese Biochemical Society [3T17e-03], English Abstract Only.

Miyagi (2008) "Regulation of Cellular Functions by Sialidase and Its Abnormalities", Journal of Japanese Biochemical Society, vol. 80, No. 1, pp. 13-23, English Abstract Only.

Itoh et al. (2018) "Development of Enzyme Drugs Derived from Transgenic Silkworms to Treat Lysosonal Diseases", Journal of Pharmaceutical Society of Japan, vol. 138, No. 7, pp. 885-893, English Abstract Only,.

International Search Report corresponding to International Application No. PCT/JP2020/026174 mailed Sep. 15, 2020 (2 pages).

International Preliminary Report on Patentability and Written Opinion corresponding to International Application No. PCT/JP2020/026174 dated Jan. 11, 2022 (4 pages).

Extended European Search Report issued Jun. 6, 2023 in European Patent Application No. 20836020.6.

Database UniProt (Online) Refseq: Feb. 19, 2014), "Predicted: Sialidase-1 from *Chrysochloris asiatica* (Cape golden mole)", XP002809505, retrieved from NCBI accession No. Refseq XP_006875727 *sequence*.

J.E. Kwak et al., "Biochemical and molecular characterization of novel mutations in GLB1 and NEU1 in patient cells with lysosomal storage disorders", Biochemical and Biophysical Research Communications, 457(4), pp. 554-560 (Jan. 2015).

* cited by examiner

*Primary Examiner* — Sharmila G Landau
*Assistant Examiner* — Ashley T White
(74) *Attorney, Agent, or Firm* — Fox Rothschild LLP

(57) ABSTRACT

Provided are a modified-type neuraminidase, a gene encoding the modified-type neuraminidase, a combination of the modified-type neuraminidase and cathepsin A, a combination of the gene encoding the modified-type neuraminidase and a gene encoding cathepsin A, a vector including said genes, and a pharmaceutical composition containing same. The pharmaceutical composition can be used for the therapy of lysosomal storage disease.

20 Claims, 12 Drawing Sheets

Specification includes a Sequence Listing.

[FIG. 1]
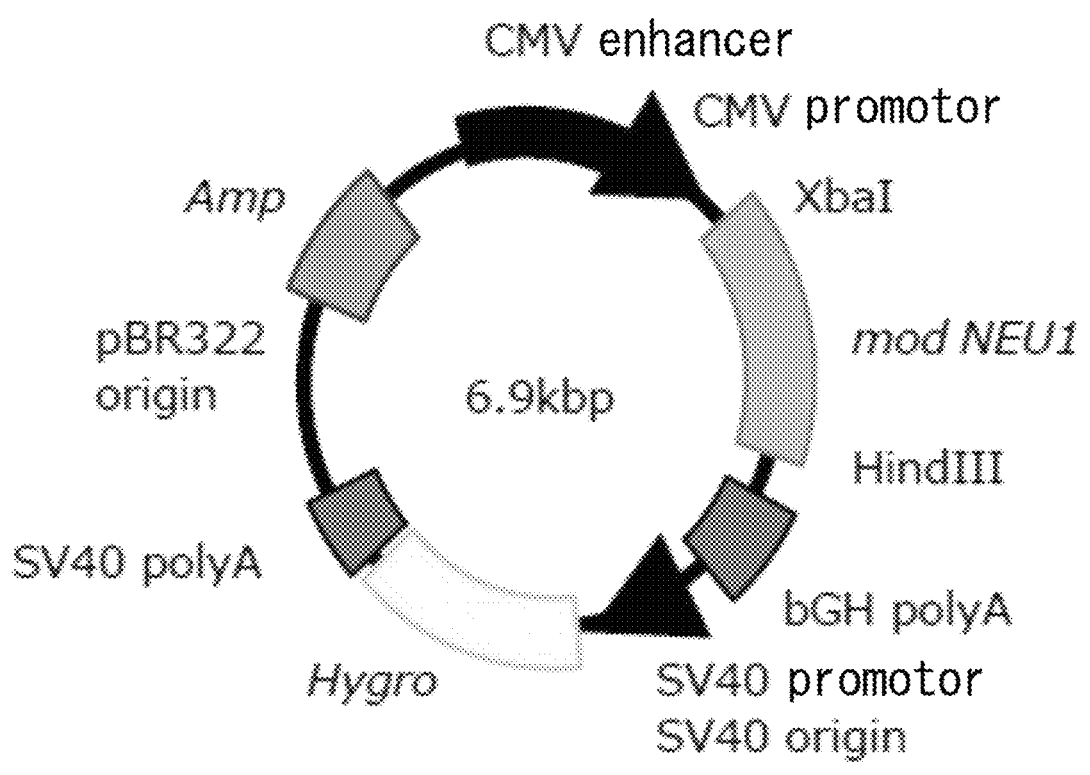

[FIG. 2]
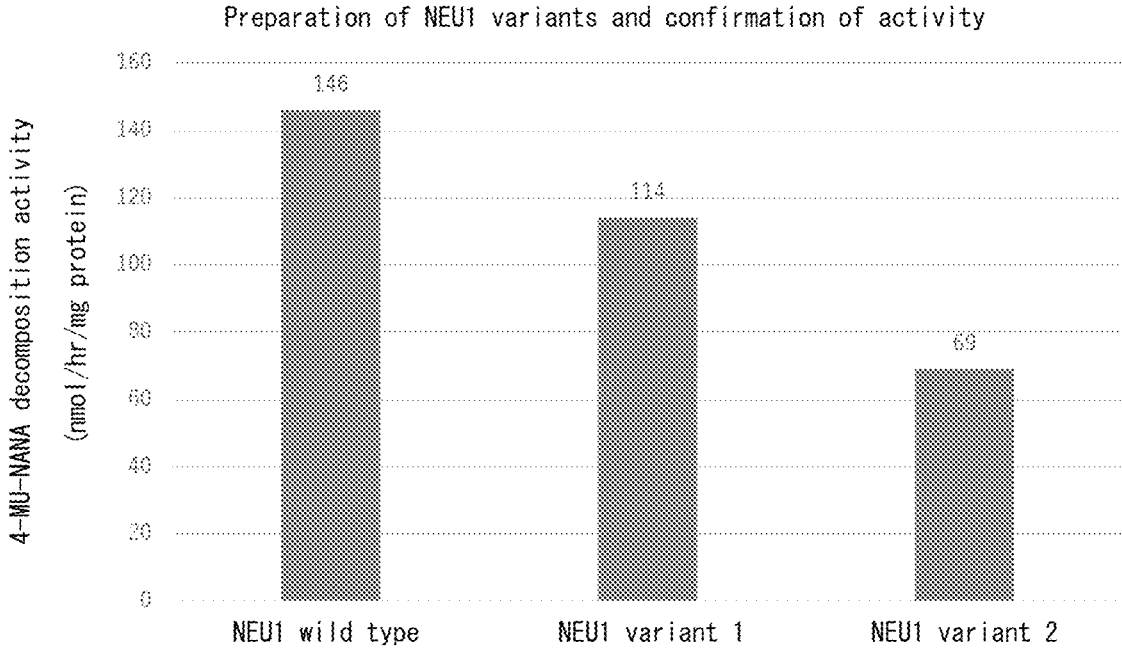
Preparation of NEU1 variants and confirmation of activity
[FIG. 3]
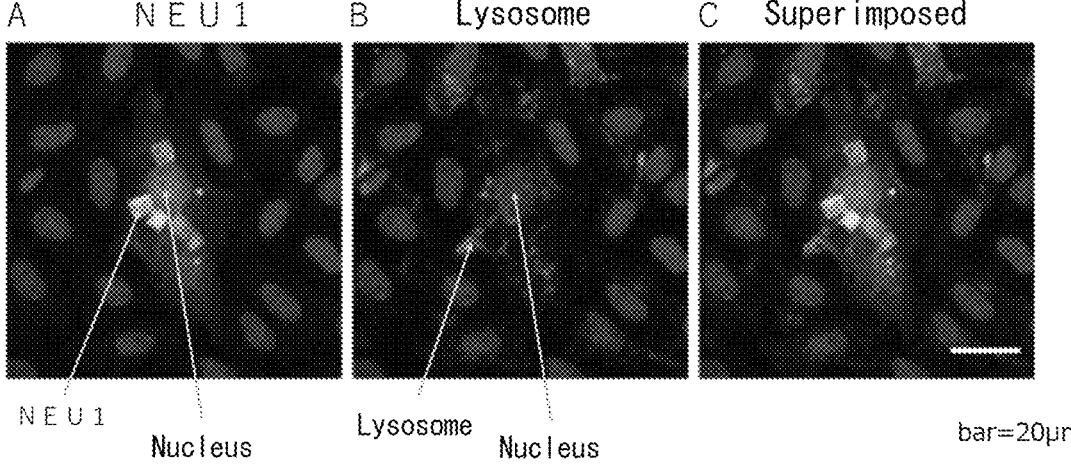

[FIG. 4]
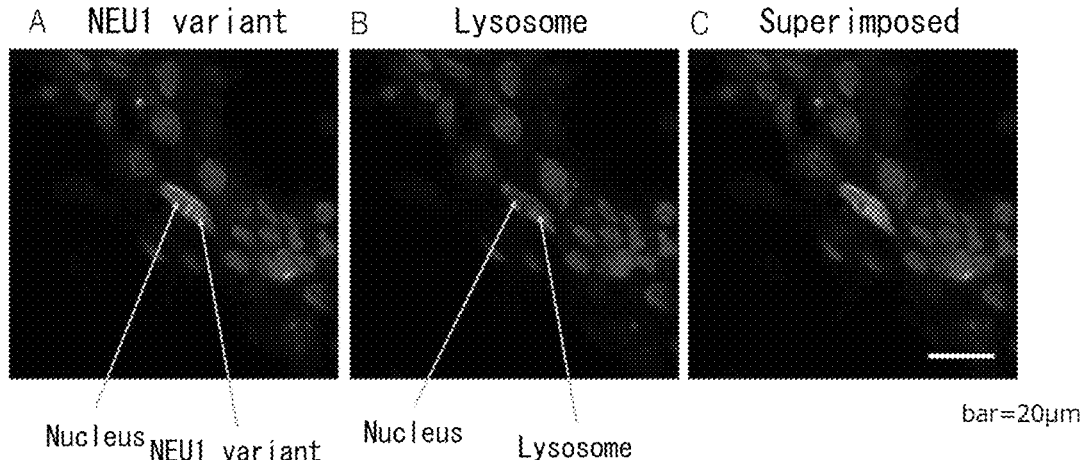
[FIG. 5]
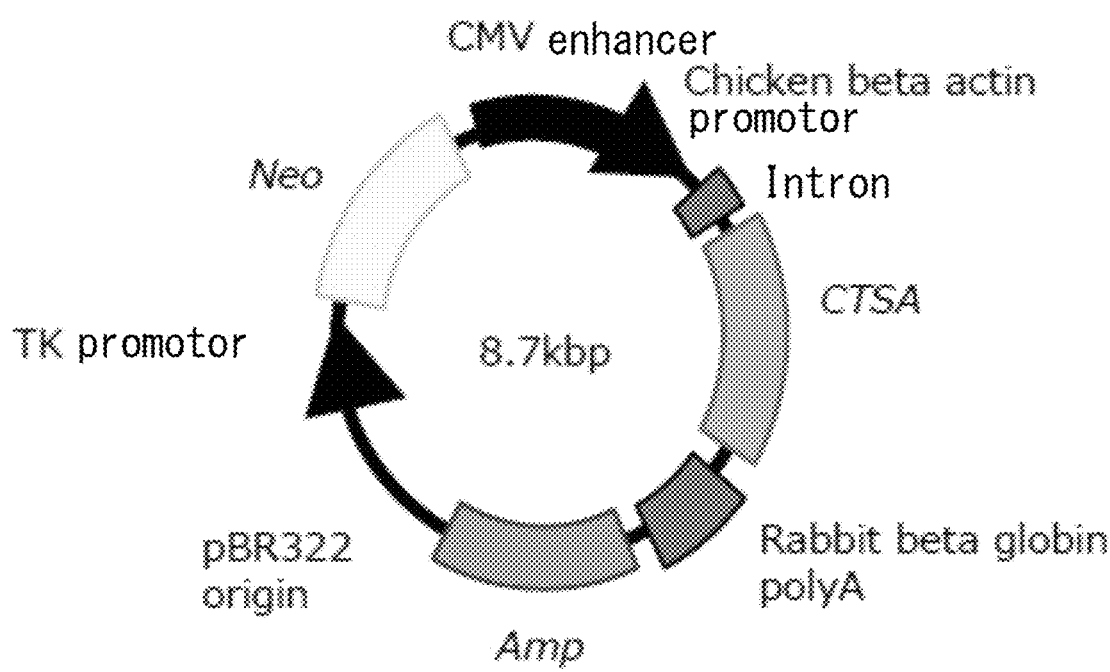

[FIG. 6]
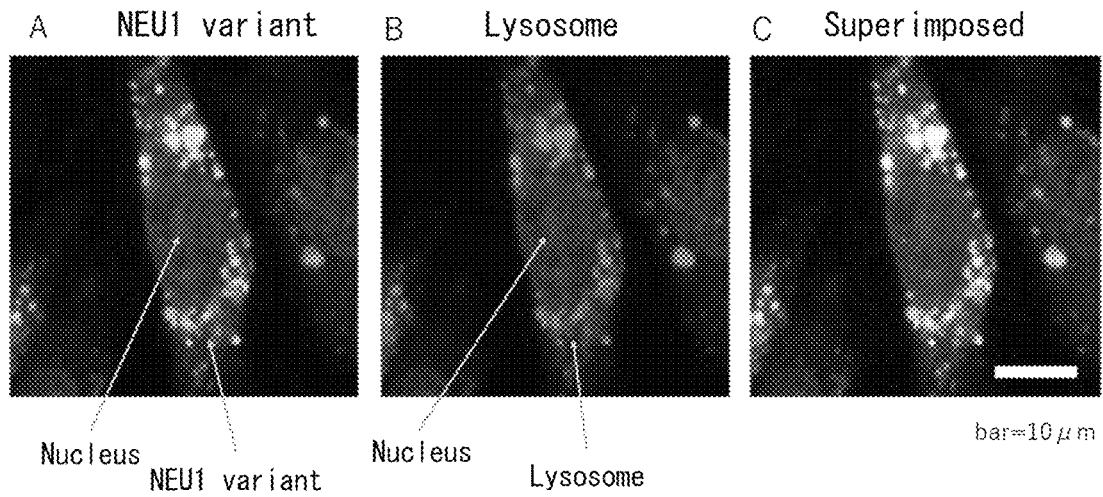
A    NEU1 variant      B    Lysosome      C    Superimposed
bar=10μm
Nucleus
NEU1 variant
Nucleus
Lysosome
[FIG. 7]
pBI-CMV1 *CTSA+ mod NEU1*
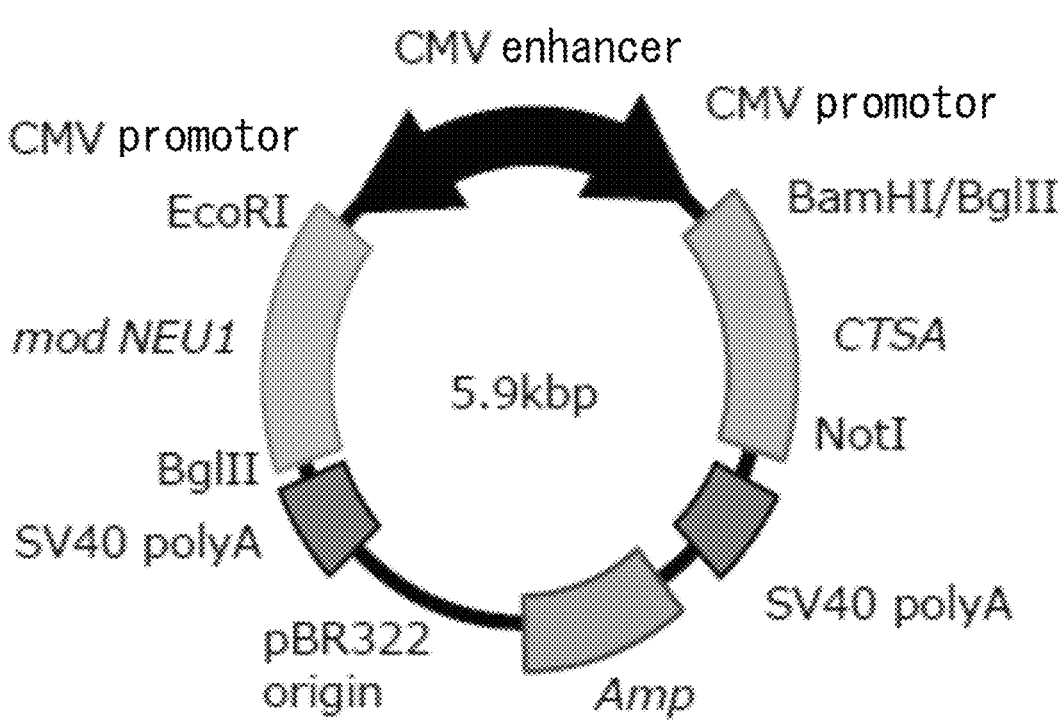
CMV enhancer
CMV promotor
CMV promotor
EcoRI
BamHI/BglII
*mod NEU1*
*CTSA*
5.9kbp
NotI
BglII
SV40 polyA
SV40 polyA
pBR322 origin
*Amp*

[FIG. 8]
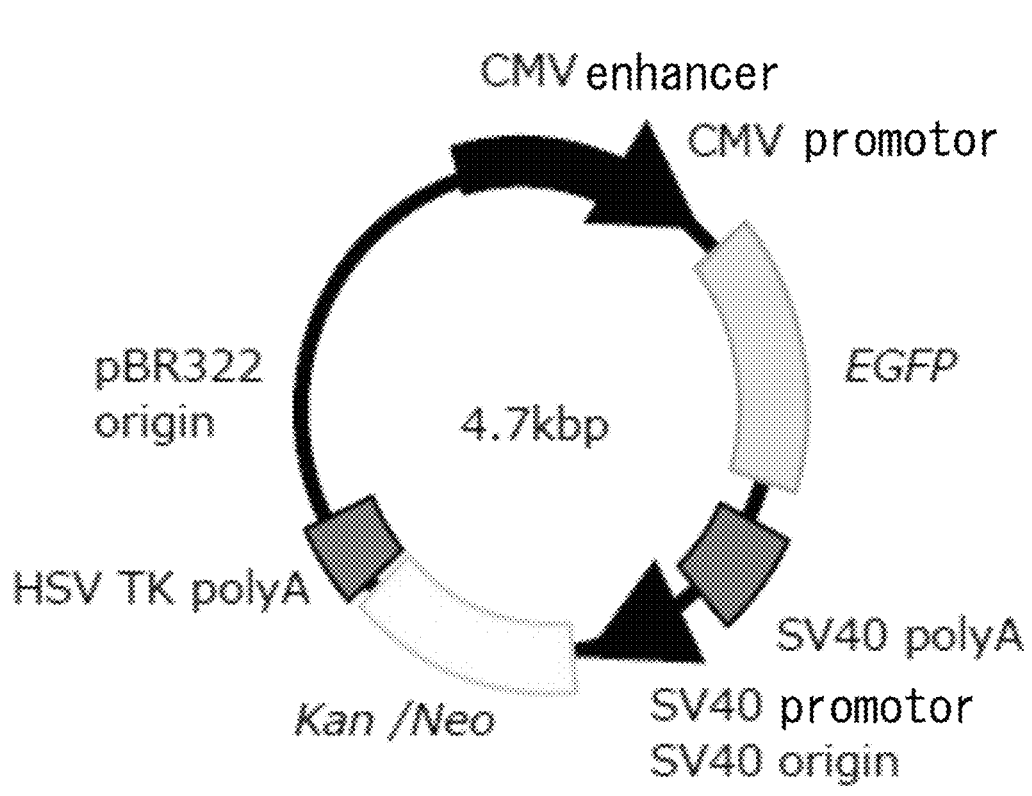

[FIG. 9]
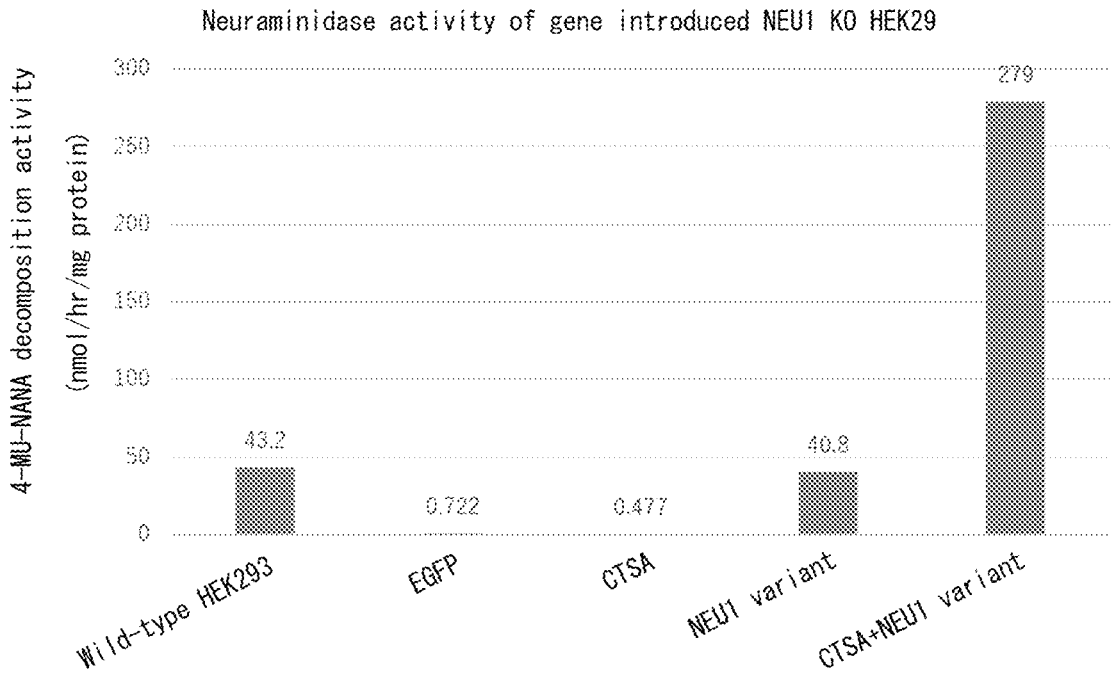
[FIG. 10]
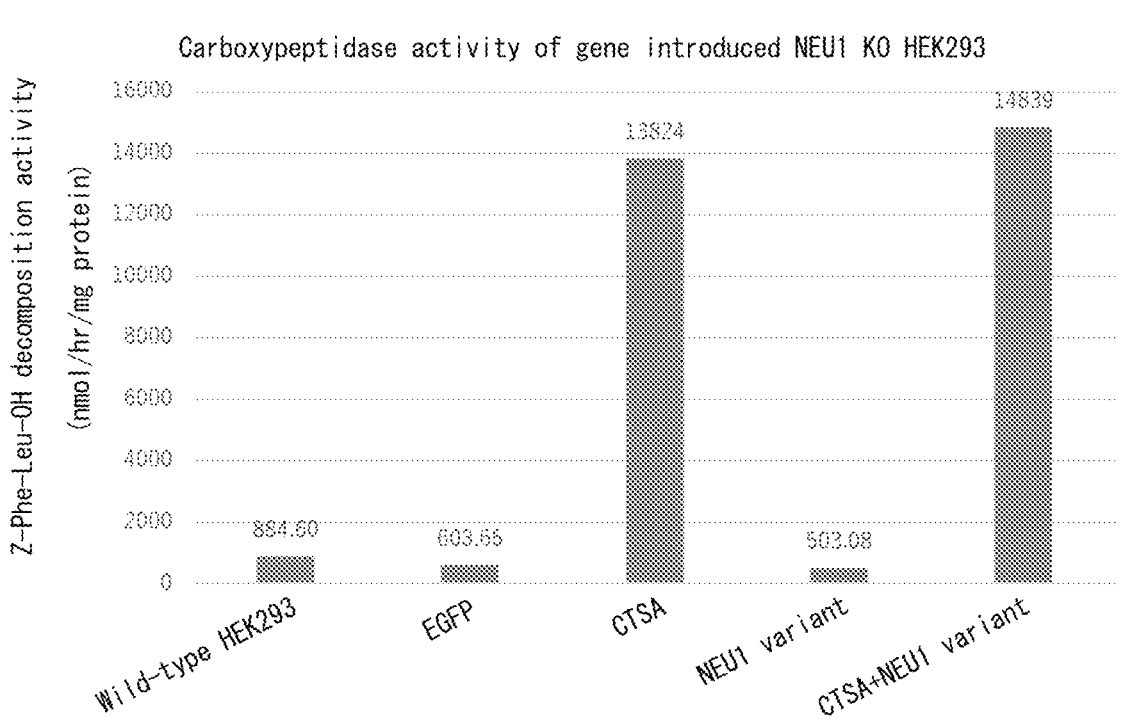

[FIG. 11]
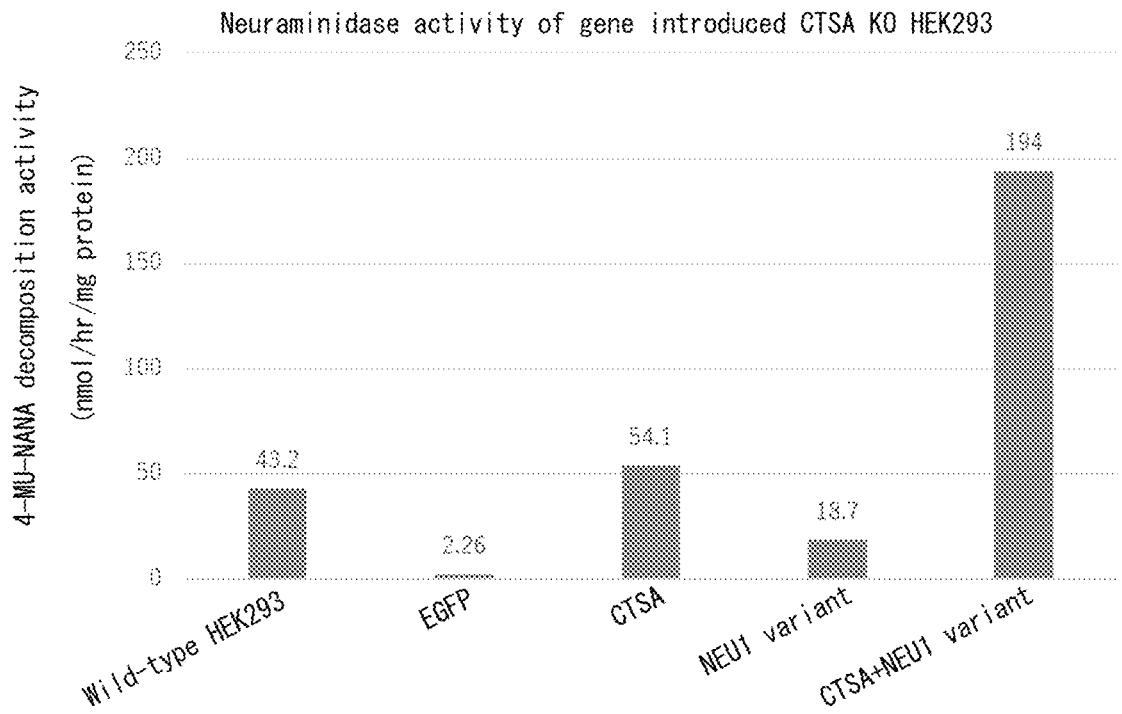
[FIG. 12]
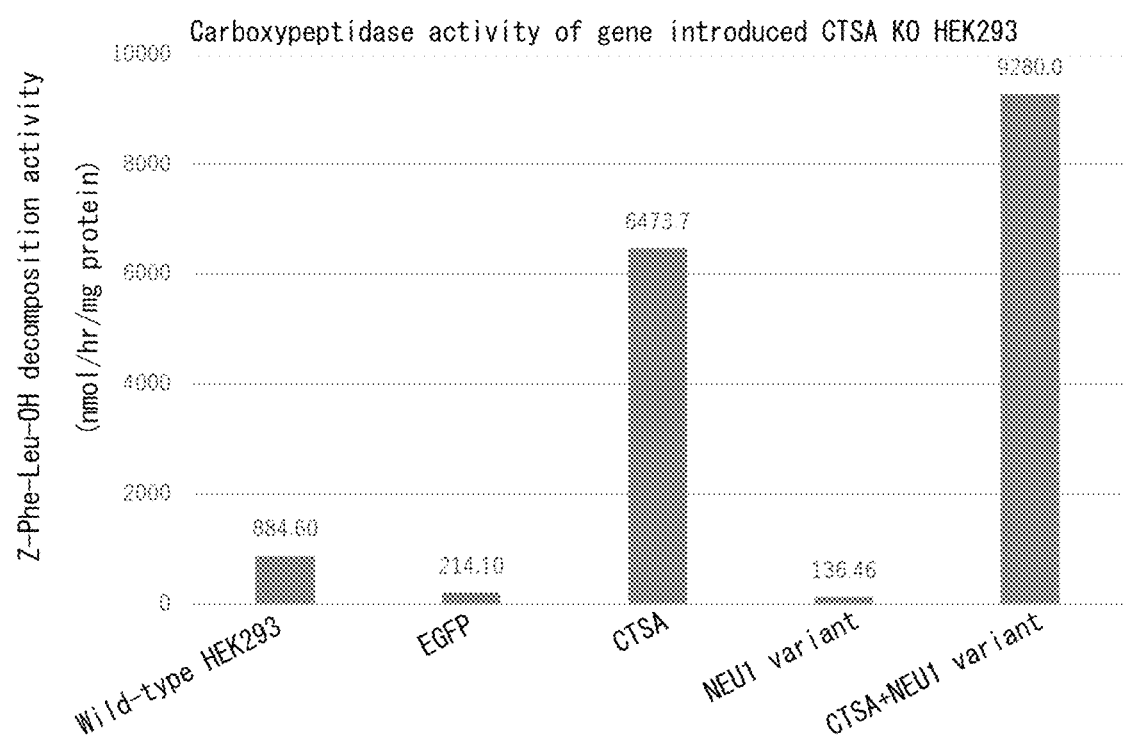

[FIG. 13]
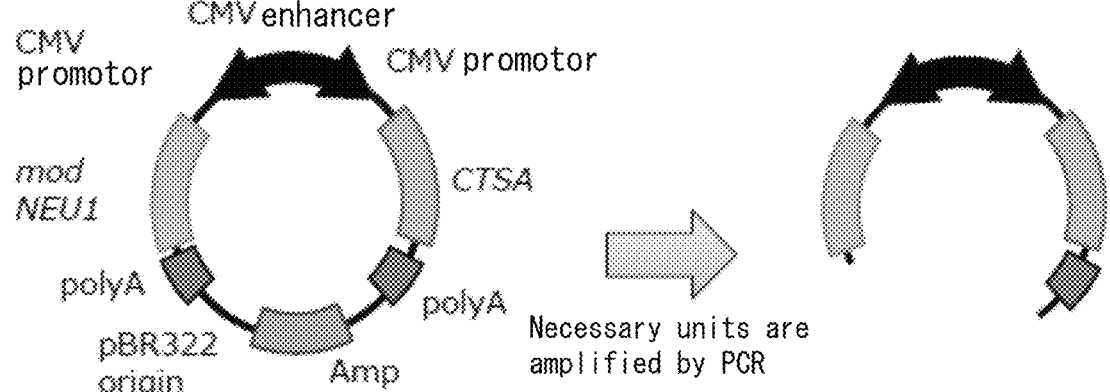
[FIG. 14]
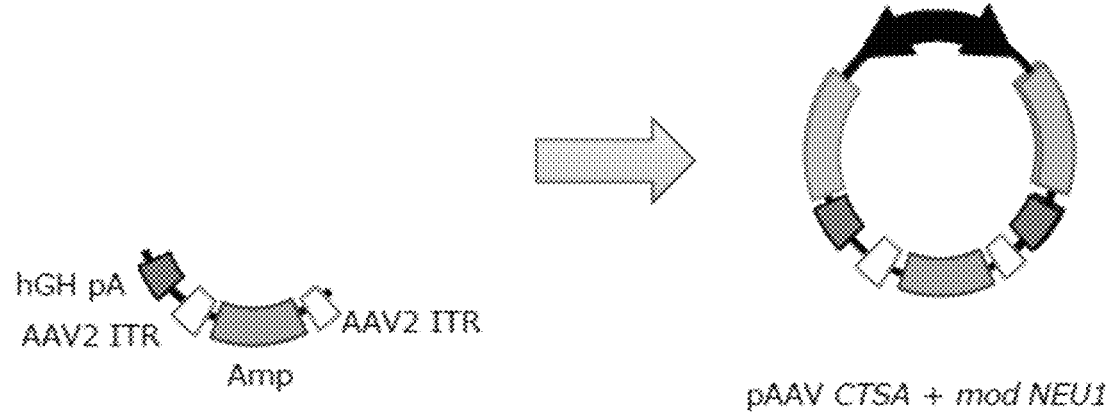

[FIG. 15]
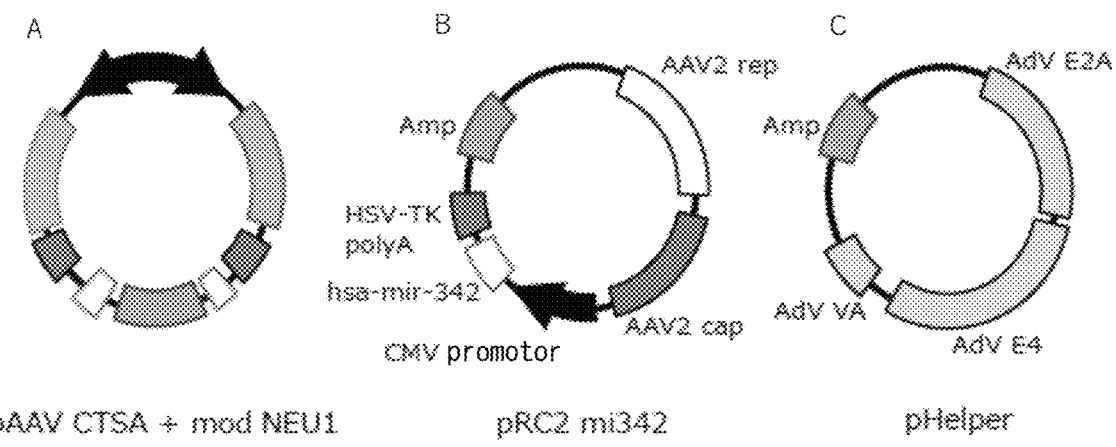
A                          B                          C
pAAV CTSA + mod NEU1        pRC2 mi342                 pHelper
[FIG. 16]
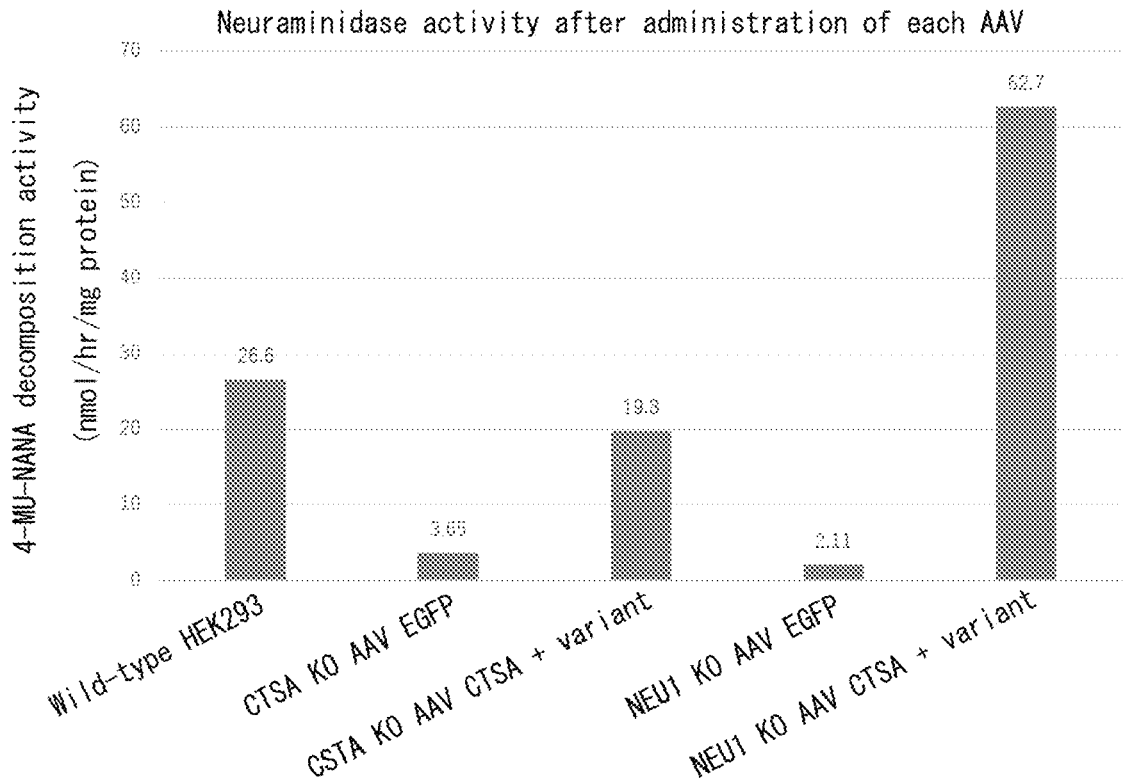
Neuraminidase activity after administration of each AAV

[FIG. 17]
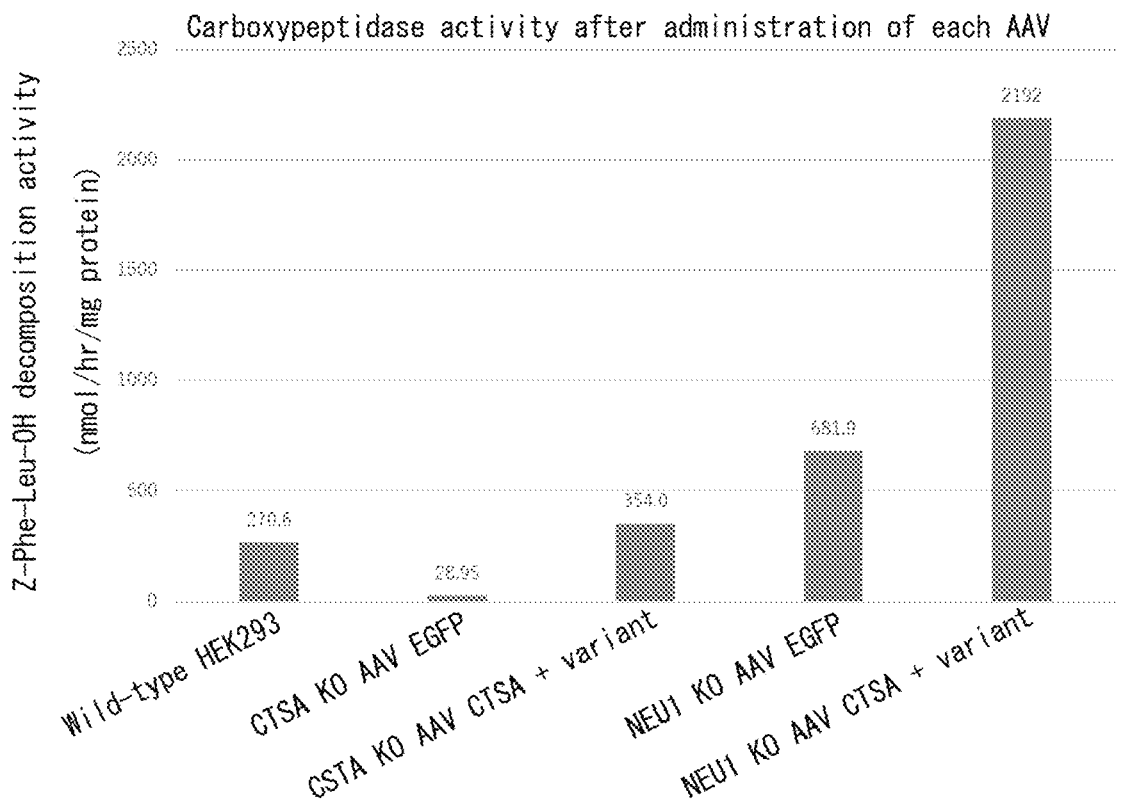

[FIG. 18]
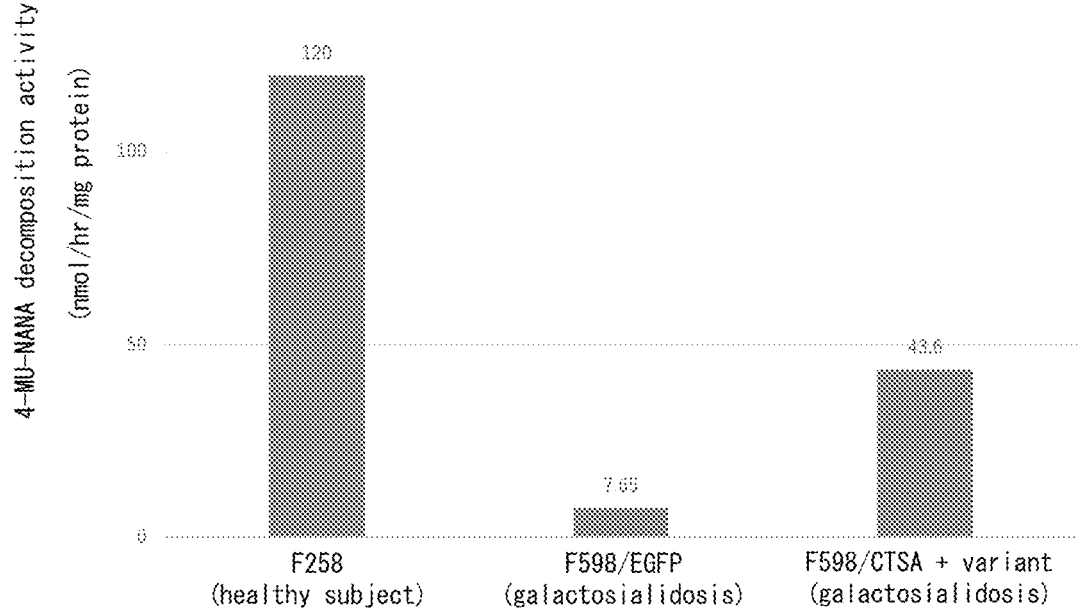
Neuraminidase activity of skin fibroblast after administration of each AAV
[FIG. 19]
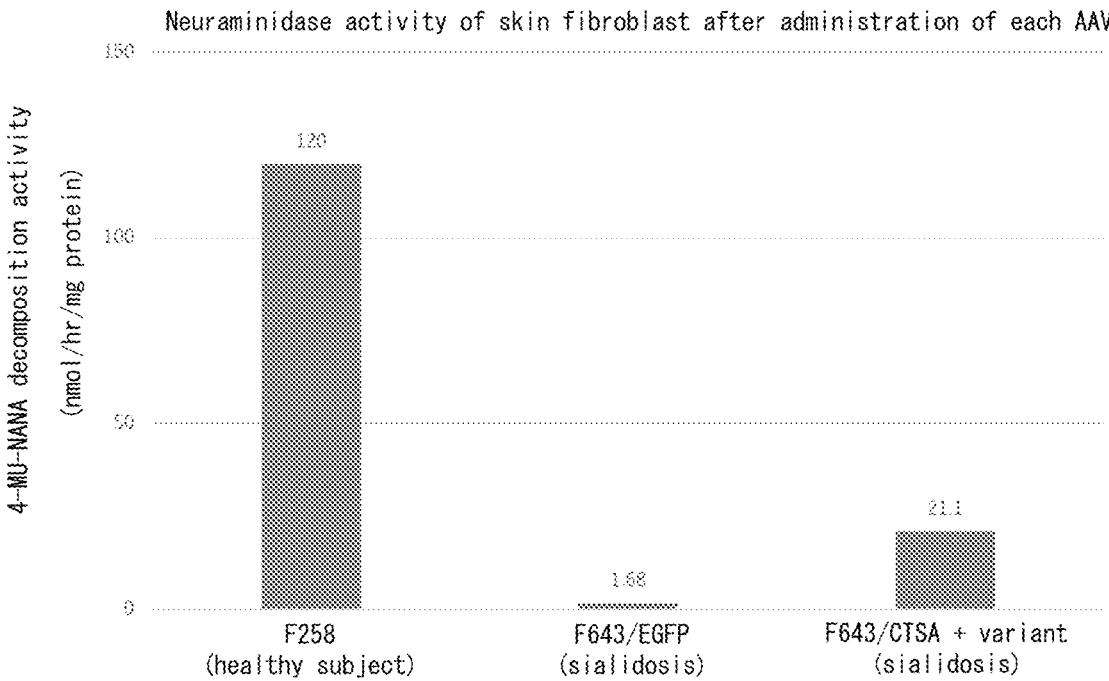
Neuraminidase activity of skin fibroblast after administration of each AAV

[FIG. 20]
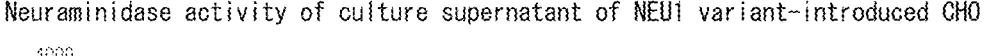
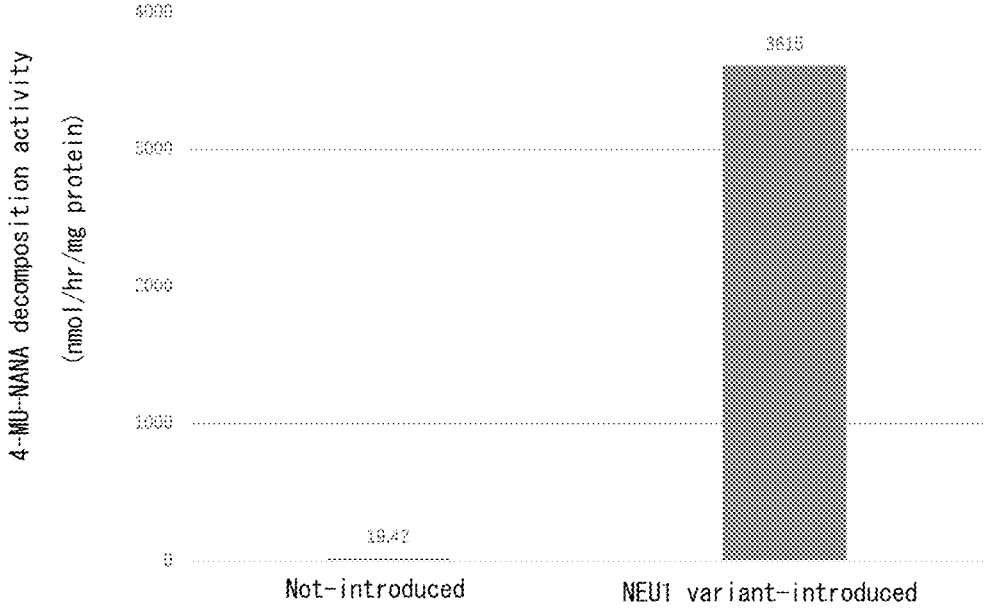
Neuraminidase activity of culture supernatant of NEU1 variant-introduced CHO

MODIFIED NEURAMINIDASE

RELATED APPLICATIONS

This application is a national stage application filed under 35 U.S.C. § 371, of International Patent Application No. PCT/JP2020/026174 filed Jul. 3, 2020, which claims the benefit of and priority to Japanese Patent Application No. 2019-126376 filed Jul. 5, 2019, the entire contents of which are hereby expressly incorporated by reference herein.

INCORPORATION-BY-REFERENCE OF SEQUENCE LISTING

The contents of the sequence listing text file named "048869-520N01US_Sequence_Listing.txt", which was created on Jul. 5, 2019 and is 28,672 bytes in size, is hereby incorporated by reference in its entirety.

TECHNICAL FIELD

The present invention relates to a modified neuraminidase, and a gene encoding the modified neuraminidase. The present invention also relates to a combination of modified neuraminidase and cathepsin A, a combination of gene encoding modified neuraminidase and gene encoding cathepsin A. The present invention also relates to a vector containing any of these genes. The present invention also relates to a pharmaceutical composition containing any of the foregoing.

BACKGROUND ART

Neuraminidase (N-acetyl-α-neuraminidase, also referred to as lysosomal sialidase) is a type of glycosidase which removes a terminal sialic acid residue of a sugar chain by hydrolysis. It is known that four types of neuraminidases are present in human cells. Among them, neuraminidase 1 (hereinafter, also referred to as NEU1) has been actively studied as a target enzyme for two clinically similar neuro-degenerative lysosomal storage diseases, i.e. sialidosis and galactosialidosis. In addition, Patent Document 1 describes that lack of NEU1 is also associated with amyloidosis, and Non-Patent Document 1 describes that NEU1 is also associated with cancer metastasis and infiltration.

The lysosomal storage disease (also referred to as lyso-somal disease) is a group of diseases of inborn errors of metabolism based on a mutation of a gene encoding an acidic hydrolase (lysosomal enzyme) or a cofactor contained in a lysosome which is an intracellular small organ (organelle) that decompose and metabolize biomolecules inside and outside a cell. The lysosomal strage disease was an incurable disease. However, after 1990, enzyme replacement therapy (ERT) has come into practical use, and clinically applied to nine types of patients having mainly peripheral symptoms (Non-Patent Document 2). The enzyme replacement therapy is a method of continuous intravenous administration of a recombinant enzyme preparation secreted and purified from a strain of cultured animal or plant cells, into which a normal human lysosome enzyme gene is introduced, to a patient on a regular basis (every one to two weeks). However, the enzyme replacement therapy has a problem that applicable diseases are limited. Thus, a further method for treatment of lysosomal storage diseases is required.

PRIOR ART DOCUMENTS

Patent Documents

Patent Document 1: JP 2014-526904 A

Non Patent Literature

Non-Patent Document 1: Journal of Japanese Biochemical Society, Vol. 80, No. 1, 13-23, 2008
Non-Patent Document 2: Journal of Pharmaceutical Society of Japan, Vol. 138, No. 7 (2018)

SUMMARY OF INVENTION

Problems to be Solved by Invention

The present inventors have conducted studies on gene therapy using human neuraminidase 1, and have found that overexpression of human neuraminidase 1 causes intracellular crystals, resulting in breakage of cells. Accordingly, application of human neuraminidase 1 to gene therapy has been found to damage cell and involve risk. One of objects of the present invention is to provide a modified neuraminidase which does not crystallize in the cell and may be used for gene therapy. Another object of the present invention is to provide means for co-localizing neuraminidase 1 with a lysosome.

The present inventors have extensively studied for solving the above-described problems, and have found that certain modified neuraminidase 1 does not crystallize even when overexpressed in cells. It has been also found that when cathepsin A (CTSA) is overexpressed, neuraminidase 1 co-localizes with lysosomes. The present invention has been completed based on the above-described findings.

Specifically, the present invention relates to:
(1) a modified neuraminidase including an amino acid sequence having a sequence identity of 80% to the amino acid sequence set forth in SEQ ID NO: 1, wherein the amino acid sequence has the following mutations with respect to the amino acid sequence set forth in SEQ ID NO: 1:
(i) W173N or K175S mutation; and
(ii) K358N mutation;
(2) a modified neuraminidase having a sequence set forth in SEQ ID NO: 2 or SEQ ID NO: 3;
(3) a nucleic acid encoding the modified neuraminidase of (1) or (2);
(4) a vector including the nucleic acid of (3);
(5) the vector of (4), which is an AAV vector;
(6) the vector of (4) or (5), further including a nucleic acid encoding cathepsin A;
(7) a pharmaceutical composition including the modified neuraminidase of (1) or (2) or the vector of any one of (4) to (6); and
(8) the pharmaceutical composition of (7), for treatment of a disease associated with deletion or attenuation of neuraminidase 1 activity.

The present invention enables to provide a modified neuraminidase 1 which does not crystallize or only slightly crystallizes even when overexpressed. Use of the neuraminidase 1 in combination with a cathepsin A enables co-localization of the neuraminidase 1 with a lysosome.

BRIEF DESCRIPTION OF DRAWINGS

FIG. 1 is a diagram showing an example of a plasmid which expresses a NEU1 variant.

FIG. 2 is a diagram showing neuraminidase activity of NEU1 variants 1 and 2 in comparison with wild-type NEU1.

FIG. 3 is a diagram showing the results of immunostaining when wild-type NEU1 is overexpressed. A: NEU1, B: lysosome, C: superimposed picture of A and B. The nuclei are stained with Hoechst 33258, NEU1 is stained with anti-NEU1, and the lysosome is stained with Lysotracker.

FIG. 4 is a diagram showing the results of immunostaining when the NEU1 variant 1 is overexpressed. A: NEU1, B: lysosome, C: superimposed picture of A and B. The nuclei are stained with Hoechst 33258, NEU1 is stained with anti-NEU1, and the lysosome is stained with Lysotracker.

FIG. 5 is a diagram showing a plasmid used in preparation of CTSA-overexpressing cells.

FIG. 6 is a diagram showing the results of immunostaining when the NEU1 variant 1 is overexpressed in the CTSA-overexpressing cells. A: NEU1, B: lysosome, C: superimposed picture of A and B. The nuclei are stained with Hoechst 33258, NEU1 is stained with anti-NEU1, and the lysosome is stained with Lysotracker.

FIG. 7 is a diagram showing an example of a CTSA+ NEU1 variant coexpression plasmid.

FIG. 8 shows a plasmid expressing EGFP used as a negative control.

FIG. 9 shows neuraminidase activity when each plasmid is introduced into NEU1 knockout HEK293 cells.

FIG. 10 shows carboxypeptidase activity when each plasmid is introduced into NEU1 knockout HEK293 cells.

FIG. 11 shows neuraminidase activity when each plasmid is introduced into CTSA knockout HEK293 cells.

FIG. 12 shows carboxypeptidase activity when each plasmid is introduced into CTSA knockout HEK293 cells.

FIG. 13 is a diagram showing a procedure for preparing a CTSA+NEU1 variant coexpression AAV vector.

FIG. 14 is a diagram showing a procedure for preparing a CTSA+NEU1 variant coexpression AAV vector.

FIG. 15 shows a vector used in amplification of a CTSA+ NEU1 variant coexpression AAV vector.

FIG. 16 is a diagram showing neuraminidase activity when an EGFP expression vector (negative control) and a CTSA+NEU1 variant coexpression AAV vector are administered to various HEK293 cells.

FIG. 17 is a diagram showing carboxypeptidase activity when an EGFP expression vector (negative control) and a CTSA+NEU1 variant coexpression AAV vector are administered to various HEK293 cells.

FIG. 18 is a diagram showing neuraminidase activity of skin fibroblasts of a healthy person, and neuraminidase activity when an EGFP expression vector (negative control) or a CTSA+NEU1 variant coexpression AAV vector is administered to skin fibroblasts derived from a galactosialidosis patient.

FIG. 19 is a diagram showing neuraminidase activity of skin fibroblasts of a healthy person, and neuraminidase activity when an EGFP expression vector (negative control) or a CTSA+NEU1 variant coexpression AAV vector is administered to skin fibroblasts derived from a sialidosis patient.

FIG. 20 is a diagram showing neuraminidase activity of a culture supernatant of NEU1 variant-introduced CHO cells.

MODE FOR CARRYING OUT INVENTION

In one aspect, the present invention provides a modified neuraminidase. In a further aspect, the present invention provides a nucleic acid encoding a modified neuraminidase.

The modified neuraminidase of this aspect includes a sequence in which W and K at amino acid positions 173 and 175, respectively, are mutated or K at amino acid position 358 is mutated in wild-type neuraminidase 1 set forth in SEQ ID NO: 1. More specifically, the modified neuraminidase includes W173N and K175S mutations, or K358N mutation. In one embodiment, the modified neuraminidase of this aspect has the above-described mutations, and includes or consists of a sequence having a sequence identity of about 75% or more, e.g. about 80% or more, about 85% or more, about 90% or more, about 91% or more, about 92% or more, about 93% or more, about 94% or more, about 95% or more, about 96% or more, about 97% or more, about 98% or more, or about 99% or more to an amino acid sequence set forth in SEQ ID NO: 1. In a certain embodiment, the modified neuraminidase of this aspect has the above-described mutations, and further includes or consists of an amino acid sequence in which one or more, e.g. 1 to about 40, 1 to about 30, 1 to about 20, 1 to about 10, 1 to about 5, for example 1, 2, 3, 4 or 5, or 1 to 4, for example 1, 2, or 4 amino acids are substituted, inserted, deleted and/or added in an amino acid sequence set forth in SEQ ID NO: 1. In a further embodiment, the modified neuraminidase of this aspect includes or consists of an amino acid sequence set forth in SEQ ID NO: 2 or SEQ ID NO: 3.

Examples of the nucleic acid encoding the modified neuraminidase of this aspect include nucleic acids encoding the modified neuraminidase. More specific examples include nucleic acids including mutations at two or more positions among positions 517 to 519 and positions 523 to 525, or a mutation at position 1074, in a nucleic acid encoding wild-type neuraminidase 1 set forth in SEQ ID NO: 4. More specific examples include nucleic acids including a mutation of positions 517 to 519 to AAT or AAC, positions 523 to 525 to TCT, TCC, TCA, TCG, AGT or AGC, or position 1074 to T or C. In a certain embodiment, the nucleic acid encoding the modified neuraminidase of this aspect includes or consists of a sequence having the above-described mutations and having a sequence identity of about 75% or more, e.g. about 80% or more, about 85% or more, about 90% or more, about 91% or more, about 92% or more, about 93% or more, about 94% or more, about 95% or more, about 96% or more, about 97% or more, about 98% or more, or about 99% or more to a nucleic acid sequence set forth in SEQ ID NO: 4. In a certain embodiment, the nucleic acid encoding the modified neuraminidase of this aspect includes or consists of a nucleic acid sequence having the above-described mutation and having substitution, insertion, deletion and/or addition of one or more, e.g. 1 to about 40, 1 to about 30, 1 to about 20, 1 to about 10, 1 to about 5, for example 1, 2, 3, 4 or 5, or 1 to 4, for example 1, 2, 3 or 4 amino acids, in a nucleic acid sequence set forth in SEQ ID NO: 4. In a further embodiment, the nucleic acid encoding the modified neuraminidase of this aspect includes or consists of a nucleic acid sequence set forth in SEQ ID NO: 5 or SEQ ID NO: 6.

The identity of the nucleotide sequence or the amino acid sequence may be determined using an internet-based homology search site (e.g. a homology search may be conducted using FASTA, BLAST, PSI-BLAST, and SEARCH at the website of European Bioinformatics Institute (EBI): http://www.ebi.ac.uk/Tools/sss/). In addition, a search may be conducted using BLAST at National Center for Biotechnology Information (NCBI) (e.g. the BLAST page at the NCBI website; https://blast.ncbi.nlm.nih.gov/Blast.cgi; Altschul, S F et al., J. Mol. Biol., 1990, 215 (3): 403-10; Altschul, S. F. & Gish, W., Meth. Enzymol., 1996, 266: 460-480; Altschul, S F et al., Nucleic Acids Res., 1997, 25: 3389-3402).

As used herein, the term "nucleic acid" refers to a molecule formed by polymerization of nucleotides, and includes oligonucleotide and polynucleotide. The "nucleic acid" includes single-stranded or double-stranded DNA. Further, the "nucleic acid" includes those formed only of natural nucleotides, those containing unnatural bases, nucleotides and nucleosides in part, or synthetic nucleic acids. Typically, the nucleic acid is DNA.

The modified neuraminidase of this aspect may be a protein subjected to any of various modifications such as physiological modification with sugar chain etc., labeling with, for example, fluorescence and radioactive substance, and fusion with another protein. In addition, the modified neuraminidase may be one subjected to oxidation of —SH groups at cysteine residues (e.g. conversion to sulfo group), glutathionylation, nitrosylation, alkylation, or bonding to maleimide for the purpose of, for example, stabilizing the properties and structure of proteins during production and purification, and suppressing intermolecular disulfide bonds. Any of these may be used as a modified neuraminidase of this aspect as long as they are functionally equivalent.

The method for preparing the modified neuraminidase of this aspect is not particularly limited, and examples include recombinant expression (e.g., mammalian cell, yeast, *Escherichia coli* and insect cell) and synthesis using a cell-free system. Examples thereof include a method in which a nucleic acid having a nucleic acid sequence encoding a signal sequence appropriate to a host and a nucleic acid sequence encoding a modified neuraminidase of this aspect are introduced into host cells and the product are collected from a culture supernatant after recombinant expression; a method in which a nucleic acid having a nucleic acid sequence encoding a modified neuraminidase is introduced into host cells, and the cells are disrupted and collected after recombinant expression; and a method in which a nucleic acid having a nucleic acid sequence encoding a modified neuraminidase is provided as a template, and synthesis is performed in a cell-free system. The cell used for these methods are not particularly limited, and examples thereof include HEK293 cell.

The obtained modified neuraminidase may be isolated from the inside of host cells or the outside of the cells (e.g. a medium) and purified as a substantially pure and homogeneous protein. For the separation and purification of the protein, common separation and purification methods which are used in purification of proteins may be used without limitation. For example, a protein may be isolated and purified by appropriately selecting and/or combining a chromatographic column, a filter, ultrafiltration, salting-out, solvent precipitation, solvent extraction, distillation, immuno-precipitation, SDS-polyacrylamide gel electrophoresis, an isoelectric focusing method, dialysis, and recrystallization.

In another aspect, the present invention provides a vector containing a nucleic acid encoding a modified neuraminidase. Examples of the vector include, but are not limited to, plasmid vector, retrovirus vector, lentivirus vector, adenovirus vector, adeno-associated virus vector, Sendai virus vector, Sendai virus envelope vector and papillomavirus vector. Preferred examples include retroviral vector, lentiviral vector and adeno-associated virus (AAV) vector. In a more specific embodiment, the vector is an AAV vector. AAVs include, but are not limited to, AAV1, AAV2, AAV3 (including 3A and 3B), AAV4, AAV5, AAV6, AAV7, AAV8, AAV9, AAV10, AAV11, bird AAV, bovine AAV, dog AAV, horse AAV and sheep AAV, as well as any other AAV which is unknown or will be discovered later. In a certain embodiment, the AAV vector is AAV2. The vector may contain a promoter DNA sequence which effectively induces gene expression, a factor which controls gene expression, and a molecule necessary to maintain the stability of DNA.

In a certain embodiment, the vector of this aspect further include a nucleic acid encoding cathepsin A. Specific examples include nucleic acids encoding a sequence including or consisting of a sequence having a sequence identity of about 75% or more, e.g. about 80% or more, about 85% or more, about 90% or more, about 91% or more, about 92% or more, about 93% or more, about 94% or more, about 95% or more, about 96% or more, about 97% or more, about 98% or more or about 99% or more to an amino acid sequence set forth in SEQ ID NO: 13; nucleic acids encoding a sequence including or consisting of an amino acid sequence having substitution, insertion, deletion and/or addition of one or more, e.g. 1 to about 40, 1 to about 30, 1 to about 20, 1 to about 10, 1 to about 5, for example 1, 2, 3, 4 or 5, or 1 to 4, for example 1, 2, 3 or 4 amino acids, in an amino acid sequence set forth in SEQ ID NO: 13; nucleic acids encoding a sequence including or consisting of an amino acid sequence set forth in SEQ ID NO: 3; nucleic acids having a sequence identity of about 75% or more, e.g. about 80% or more, about 85% or more, about 90% or more, about 91% or more, about 92% or more, about 93% or more, about 94% or more, about 95% or more, about 96% or more, about 97% or more, about 98% or more or about 99% or more to a nucleic acid sequence set forth as SEQ ID NO: 14; nucleic acids including or consisting of a sequence in which one or more, e.g. 1 to about 40, 1 to about 30, 1 to about 20, 1 to about 10, 1 to about 5, for example 1, 2, 3, 4 or 5, or 1 to 4, for example 1, 2, 3 or 4 nucleic acids are substituted, inserted, deleted and/or added in a nucleic acid sequence set forth in SEQ ID NO: 14; and nucleic acids including or consisting of a nucleic acid sequence set forth in SEQ ID NO: 14.

In a further aspect, the present invention provides a cell which secretes a modified neuraminidase. In a certain embodiment, the cell which secretes a modified neuraminidase also secretes cathepsin A. The cell which secretes a modified neuraminidase of this aspect is, for example, a cell having any of the above-described nucleic acid sequences. The cell which secretes a modified neuraminidase of this aspect may be prepared by, for example, introducing any of the above-described vectors.

In a further aspect, the present invention provides a pharmaceutical composition including the modified neuraminidase, a combination of the modified neuraminidase and cathepsin A, a nucleic acid encoding the modified neuraminidase, a combination of a nucleic acid encoding the modified neuraminidase and a nucleic acid encoding cathepsin A, a vector containing a nucleic acid encoding the modified neuraminidase, or a cell which secretes the modified neuraminidase.

The pharmaceutical composition of this aspect may be formulated according to a conventional method (see, for example, Remington's Pharmaceutical Science, latest edition, Mark Publishing Company, Easton, USA), and contains pharmaceutically acceptable carrier and additive. Examples thereof include surfactant, excipient, colorant, flavor, preservative, stabilizer, buffer, suspending agent, tonicity agent, binder, disintegrant, lubricant, fluidity promoter and flavoring agent. However, it is not limited to these, and other commonly used carriers may be appropriately used. Specific examples thereof include light anhydrous silicic acid, lactose, crystalline cellulose, mannitol, starch, carmellose calcium, carmellose sodium, hydroxypropyl cellulose, hydroxypropyl methyl cellulose, polyvinyl acetal diethylaminoacetate, polyvinyl pyrrolidone, gelatin, medium-chain fatty acid triglyceride, polyoxyethylene hydrogenated castor oil 60, sucrose, carboxymethyl cellulose, corn starch and inorganic salt.

Examples of a method for administering the pharmaceutical composition of this aspect include oral administration and parenteral administration, and specific examples of such administration methods include injection administration, nasal administration, pulmonary administration and transdermal administration. As an example of injection administration, the pharmaceutical composition of this aspect may be administered systemically or locally (e.g. subcutaneous, intradermal, skin surface, eyeball or palpebral conjunctiva, nasal mucosa, oral cavity, gastrointestinal mucosa, vaginal/intrauterine mucosa, intraperitoneal, intrathecal (e.g. intrathecal or lumbar intramedullary) or intraventricular) by intravenous injection, intramuscular injection, intraperitoneal injection, or subcutaneous injection.

In addition, the administration method may be appropriately selected depending on, e.g. patient's age and symptom. When the modified neuraminidase is administered, for example, the dose may be selected within a range of about 0.0000001 mg to about 1000 mg per 1 kg of body weight per administration. Alternatively, for example, the dose may be selected within a range of about 0.00001 to about 100000 mg/body per patient. When a gene therapy vector containing a cell secreting the modified neuraminidase or DNA encoding the modified neuraminidase is administered, administration may be performed in such a manner that the amount of the modified neuraminidase is within the above-described range in a target tissue. However, the dose of the composition is not limited to those mentioned above.

The pharmaceutical composition of this aspect may be used for treatment of a disease caused by deletion or attenuation of neuraminidase 1 activity. Examples of the disease include lysosomal storage disease, amyloidosis and cancer. As a more specific example, the pharmaceutical composition of this aspect may be used for treatment of galactosialidosis or sialidosis.

As used herein, the term "patient" or "subject" includes human or non-human animals, and examples thereof include, but are not limited to, human, mouse, rat, monkey, pig, dog, rabbit, hamster and guinea pig.

As used herein, the term "treatment" refers to, for example, any of alleviation, amelioration and/or elimination, regression and/or stabilization of a symptom (e.g. it means that the symptom does not progress to a more advanced stage).

The present invention also provides the following aspects:

(1) a method for treating lysosomal storage disease, amyloidosis or cancer, preferably lysosomal storage disease, more preferably galactosialidosis or sialidosis, the method including administering the modified neuraminidase, a combination of the modified neuraminidase and cathepsin A, a nucleic acid encoding the modified neuraminidase, a combination of a nucleic acid encoding the modified neuraminidase and a nucleic acid encoding cathepsin A, a vector containing a nucleic acid encoding the modified neuraminidase, or a cell which secretes the modified neuraminidase, to a subject in need thereof;

(2) a method for treating lysosomal storage disease, amyloidosis or cancer, preferably lysosomal storage disease, more preferably galactosialidosis or sialidosis, the method including administering a composition containing the modified neuraminidase, a combination of the modified neuraminidase and cathepsin A, a nucleic acid encoding the modified neuraminidase, a combination of a nucleic acid encoding the modified neuraminidase and a nucleic acid encoding cathepsin A, a vector containing a nucleic acid encoding the modified neuraminidase, or a cell which secretes the modified neuraminidase, to a subject in need thereof;

(3) use of the modified neuraminidase, a combination of the modified neuraminidase and cathepsin A, a nucleic acid encoding the modified neuraminidase, a combination of a nucleic acid encoding the modified neuraminidase and a nucleic acid encoding cathepsin A, a vector containing a nucleic acid encoding the modified neuraminidase, or a cell which secretes the modified neuraminidase, for treatment of lysosomal storage disease, amyloidosis or cancer, preferably lysosomal storage disease, more preferably galactosialidosis or sialidosis; and (4) use of the modified neuraminidase, a combination of the modified neuraminidase and cathepsin A, a nucleic acid encoding the modified neuraminidase, a combination of a nucleic acid encoding the modified neuraminidase and a nucleic acid encoding cathepsin A, a vector containing a nucleic acid encoding the modified neuraminidase, or a cell which secretes the modified neuraminidase, in the manufacture of a medicament for treatment of lysosomal storage disease, amyloidosis or cancer, preferably lysosomal storage disease, more preferably galactosialidosis or sialidosis.

In these aspects, descriptions of the modified neuraminidase, the nucleic acid encoding the modified neuraminidase, the vector containing the nucleic acid encoding the modified neuraminidase, the cell which secretes the modified neuraminidase, form, formulation, method for administration, and the dose thereof and other embodiments are as described above.

In the case of a combination of the modified neuraminidase and cathepsin A, they may be administered either simultaneously or sequentially, or may be administered as one preparation.

The prior art documents cited herein are incorporated herein by reference in their entirety. If there is a discrepancy between the descriptions of the present specification and the cited documents, the discrepancy is resolved by the description of the present specification. As used herein, the term "about" means a range of ±10%, preferably ±5%, more preferably ±1%. A numerical value which gives a boundary value of the range is considered to be described in the present specification.

EXAMPLES

Hereinafter, the present invention will be described in detail by way of examples, which do not necessarily limit the scope of the present invention.

(Measurement Methods)

<Measurement of Neuraminidase Activity>

1. Preparation of Disrupted Cell Liquid

The medium is removed, and cells are then peeled off with PBS and recovered in a 1.5 mL tube. The cells are centrifuged at 500×g at 4° C. for 5 minutes, the supernatant was removed, and the cells are resuspended in 1 mL of PBS, and centrifuged again. The supernatant is removed, 250 μl of a lysis buffer (1% Triton X-100/150 mM NaCl/50 mM sodium acetate buffer (pH 4.5)/1 μM pepstatin A (Peptide Institute Inc.)/2 mM EDTA) is added, and the mixture is pipetted to obtain a disrupted cell liquid.

2. Quantification of Protein of Disrupted Cell Liquid

The disrupted cell liquid diluted with a lysis buffer was dispensed into each well of a 96-well plate at 5 μL. A calibration curve of the concentrations shown in the table below is prepared in the 96-well plate.

TABLE 1

| BSA concentration (mg/mL) | 0 | 0.2 | 0.4 | 0.6 | 0.8 | 1 |
|---|---|---|---|---|---|---|
| 1 mg/mL BSA | 0 | 1 | 2 | 3 | 4 | 5 |
| Milli-Q water | 5 | 4 | 3 | 2 | 1 | 0 |

Solutions A and S of DC Protein Assay Reagent (Bio-Rad) are mixed at a ratio of 50:1, 25 μL of the mixture is added to each well, 200 μL of solution B is then added, and the mixture is reacted at room temperature for 15 minutes. The absorbance at 750 nm is measured with a plate reader (Tecan) to quantify the protein.

3. Measurement of Neuraminidase Activity

The disrupted cell liquid is dispensed at 20 μL, 20 μL of a substrate solution (0.2M sodium acetate buffer (pH 4.5): 8 μL, Mili-Q water: 5 μL, 50 mg/mL BSA (Sigma Aldrich): 2 μL and 2 mM 4-MU-NANA (Carbosynth): 5 μL) is added, and the mixture is reacted at 37° C. for 30 minutes. Thereafter, 370 μL of a 0.2M glycine-NaOH buffer (pH 10.7) is added to stop the reaction. A calibration curve of the concentrations shown in the table below is prepared.

TABLE 2

| 4-MU amount (nmol) | 0 | 1 | 2 | 3 | 4 | 5 |
|---|---|---|---|---|---|---|
| 100 μM 4-MU (μL) | 0 | 10 | 20 | 30 | 40 | 50 |
| Gly-NaOH (pH 10.7) (μL) | 410 | 400 | 390 | 380 | 370 | 360 |

The fluorescence intensity is measured at an excitation wavelength of 355 nm and a fluorescence wavelength of 460 nm, and the specific activity is calculated.

<Measurement of Carboxypeptidase Activity>

The disrupted cell liquid is centrifuged at 12000×g at 4° C. for 5 minutes, and the supernatant is recovered and taken as a cell extract. The protein is quantified with the Bio-Rad DC Protein assay reagent.

1. First-Order Reaction

Twenty-five microliters of the cell extract is added to three 1.5 mL tubes. As a substrate MIX, a mixture of 12.5 μL of 0.2M NaOAc buffer (pH 5.6) and 12.5 μL of 3 mM Z-Phe-Leu (Sigma Aldrich) is added to two tubes, and as a substrate (—), a mixture of 12.5 μL of 0.2M NaOAc buffer and 12.5 μL of water instead of 3 mM Z-Phe-Leu is added to one tube. The mixture is reacted at 25° C. for 30 minutes, and then immersed in boiling water at 100° C. for 3 minutes to stop the reaction.

2. Second-Order Reaction

A calibration curve standard is prepared as shown in the table below.

TABLE 3

| 1 mM L-leucine (μL) | 0 | 5 | 10 | 15 | 20 | 25 |
|---|---|---|---|---|---|---|
| MilliQ water | 50 | 45 | 40 | 35 | 30 | 25 |
| Amount of L-leucine (nmol) | 0 | 5 | 10 | 15 | 20 | 25 |

A second-order reaction liquid is prepared by mixing 500 μL of 0.1 M potassium phosphate buffer (pH 7.0), 1.25 μL of 0.2 M N-ethylmaleimide (Sigma Aldrich), 1 μL of L-amino acid oxidase (derived from Corotalus atrox, Sigma Aldrich)/20 mM potassium phosphate (pH 7.0), 0.5 μL of peroxidase (Sigma Aldrich) and 15 μL of 10 mg/mL o-Dianisidine (Sigma Aldrich) solution per one tube, and added to each of the samples and a standard, and the mixture is incubated at 37° C. for 40 minutes. After 40 minutes, 500 μL of 6M HCl is added to each of the samples and the standard to stop the reaction. 200 μL of each of the samples and the standard to each well of a 96-well plate, and the absorbance is measured at 540 nm.

<Immunofluorescent Staining>

1. Passage to 8-Well Chamber Slide

F-10 Ham (Sigma Aldrich) with fetal bovine serum (Biosera) at final concentration of 10%, and PBS are warmed. Transfection is performed for 24 hours, a medium of CHO 24 hours after replacement of the medium is suctioned with an aspirator, and washed with 1 mL of 1×PBS. One milliliter of 0.05% trypsin-1 mM EDTA/PBS is added, and the cells are cultured at 37° C. for 2 minutes. One milliliter of F-10 Ham is added, and cells are peeled off, and fully recovered in a 15 mL tube. The cells are centrifuged at 200×g at room temperature for 5 minutes, the supernatant is removed, the cells are suspended in 1 mL of F-10 Ham, and 30 μL of the suspension is taken and added to a 1.5 mL tube. The cells are stained by adding and mixing 30 μL of 0.3% trypan blue. Cells are counted using a blood cell counting plate. The cells are added at 1×10^4 cells per well to an 8-well chamber slide (Thermo), and diluted to 300 μL with F-10 Ham.

2. Immunofluorescent Staining

When staining is performed with Lysotracker, Lysotracker Red DND-99 (Thermo) is diluted to a final concentration at 1 μM with F-10 Ham, the medium is replaced by a medium containing Lysotracker, and the cells are cultured for 1 hour. The medium is removed, the cells are washed once with PBS at 500 μM/well, and 200 μL of 4% PFA/PBS is added to perform fixation at room temperature for 30 minutes. The cells are washed three times at 500 μL/well. Five percent goat serum (Cedarlane) and 1% BSA (Sigma Aldrich)/PBS are added at 200 μL/well to perform blocking at room temperature for 1 hour. The cells are treated with a primary antibody (anti-NEU1 F-8 (Santa Cruz, diluted by 100 times), or anti-LAMP1 (abcam, diluted by 300 times)) (at 150 μL/well), and left standing at 4° C. for 16 hours. The primary antibody solution is removed, and washed with 0.1% Tween20/PBS 500 μL (×5 times). The cells are washed with 500 μL of PBS (×1 time). The cells are treated with a secondary antibody (Alexa Fluor 488 conjugated anti-mouse IgG (H+L) F(ab') 2 (CST, diluted by 1000 times) or Alexa Fluor 555 conjugated anti-rabbit IgG (H+L) F(ab') 2 (CST, diluted by 1000 times)) and Hoechst 33258 (150 μL/well) at room temperature for 1 hour. The cells are washed with 0.1% Tween20/PBS at 500 μL/well (×5 times). The cells are washed with PBS at 500 μL/well (×2 times). The cells are encapsulated with 50% glycerol/PBS, and observed with a confocal laser scanning microscope LSM700.

<SDS-Page>

1. Preparation of Separation Gel

A mixture of 3.125 mL of 30% acrylamide, 1.875 mL of 4× lower layer buffer (1.5 M Tris-HCl, pH 8.8), 2.425 mL of MilliQ water, 75 μL of 10% SDS, 25 μL of 10% APS and 5 μL of TEMED is poured to a gel plate, water-saturated butanol is deposited thereon, and the mixture is solidified at room temperature to prepare a separation gel (12.5%).

2. Preparation of Concentration Gel

A mixture of 0.65 mL of 30% acrylamide, 1.25 mL of a 4× upper layer buffer (0.5 M Tris-HCl, pH 6.8), 3.02 mL of MilliQ water, 50 μL of 10% SDS, 25 μL of 10% APS and 5 μL of TEMED is poured to a gel plate, a comb is inserted, and the mixture is solidified at room temperature to prepare a concentration gel.

3. Preparation of Sample

Four microliters of 6× sample buffer (0.3M Tris-HCl, pH 6.8, 36% glycerol, 24% SDS, 1.2% 2-mercaptoethanol and 0.012% bromophenol blue) is added to 40 μg of a disrupted cell liquid diluted to 20 μL, and the mixture is boiled for 3 minutes. Four microliters of the 6× sample buffer is added to 5 μL of biotinylated marker or prestained marker, and diluted to 24 μL with Milli-Q water. The sample is immersed in a hot water bath at 100° C. for 3 minutes.

4. Electrophoresis

An electrophoresis bath is filled with an electrophoresis buffer (25 mM Tris, 192 mM glycine, 0.1% SDS), a gel plate is set, and the electrophoresis buffer is added on the cathode side. The comb is removed, the wells are adjusted, and all the sample is applied. SDS-PAGE is performed at a constant current of 20 mA.

<Western Blotting>

The concentration gel is cut from the gel after electrophoresis, and immersed in blotting buffer (48 mM Tris, 39 mM glycine, 20% methanol) for about 15 minutes. The PVDF membrane is immersed in methanol, and then immersed in blotting buffer for 15 minutes. Filter paper (6 sheets) is immersed in blotting buffer for 15 minutes. A transblotter is moistened with transfer buffer, filter paper (3 sheets), PVDF membrane, gel and filter paper (3 sheets) are set in this order, and transfer is started. The transfer is performed at 15V for about 1 hour. The transferred PVDF membrane is taken out, and 50% Blocking ONE/TBS is added to perform blocking for 1 hour. The primary antibody solution is applied, and the mixture is reacted overnight at 4° C. Washing is performed with PBS-T (5 minutes×3 times), followed by washing with PBS twice. The secondary antibody solution is applied to the PVDF membrane. Washing is performed with PBS-T (5 minutes×3 times), followed by washing with PBS once, followed by washing with TBS once. Thereafter, in the case of HRP labeling, the membrane is immersed in Western lightning Ultra (PerkinElmer), and detection is performed with Bio-Rad Chemi Doc RXS+. In the case of AP labeling, the membrane is immersed in BCIP/NBT (Wako)/50 mM $MgSO_4$/TBS, and detection is performed.

Example 1. Preparation of Modified Neuraminidase and Confirmation of Activity 1. Amplification of Gene Encoding Wild-Type Human Neuraminidase 1

A gene encoding human neuraminidase 1 (SEQ ID NO: 4) was amplified by PCR reaction in which reaction at 94° C. for minutes was carried out once and a cycle including reactions at 94° C. for 30 seconds, at 57° C. for 30 seconds and at 68° C. for 60 seconds was carried out 35 times, using the following primers:

forward primer: TTTTTCTAGACACCATGACTGGG-GAGCGAC (SEQ ID NO: 7); and reverse primer: ATATAAGCTTTCAGAGTGTCC-CATAGA (SEQ ID NO: 8). The PCR reaction liquid was prepared by diluting 1 μL (50 pmol) of the forward primer, 1 μL (50 pmol) of the reverse primer, 1 μL (10 ng) of template plasmid (pcDNA3.1 Hygro (−) NEU1), 5 μL of 10×KOD buffer, 2 μL of 25 mM $MgSO_4$, 5 μL of 2 mM dNTPs and 1 μL of KOD plus (Toyobo) to 50 μL with Milli-Q water.

2. Preparation and Amplification of Variants 1 and 2

In addition to the above-described primers, the following primers:

```
forward primer:
                                      (SEQ ID NO: 9)
CTACCATGTTGGTAAACAGCAGCGATGATGGTGTTTC;
and reverse primer:
                                     (SEQ ID NO: 10)
GAAACACCATCATCGCTGCTGTTTACCAACATGGTAG were used for preparation of variant 1, and the
following primers:
forward primer:
                                     (SEQ ID NO: 11)
CTCATGGCGGAACGAGACAGTCC;
and reverse primer:
                                     (SEQ ID NO: 12)
GGACTGTCTCGTTCCGCCATGAG
``` were used for preparation of variant 2.

PCR amplification was performed in the same manner as in the above 1., 125 μL of ethanol and 5 μL of 2M NaCl were then added, and the mixture was centrifuged at 18000×g at 4° C. for 30 minutes. The supernatant was removed, and the remainder was dissolved in a DNA sample buffer (10 mM Tris-HCl (pH 8.0), 50 mM EDTA, 33% glycerol and 0.3% bromophenol blue). All the solution was subjected to electrophoresis with a 1% agarose gel. The major band was cut out with a Gel Extraction kit (Qiagen), and the DNA was purified. The obtained DNA fragments were mixed at an equimolar ratio. A mixture of 2 μL of 25 mM $MgSO_4$, 5 μL of 2 mM dNTPs, 5 μL of KOD plus buffer and 1 μL of KOD plus was diluted to 50 μL with water. This was amplified by PCR reaction in which reaction at 94° C. for 2 minutes was carried out once and a cycle including reactions at 94° C. for 30 seconds, at 57° C. for 30 seconds and at 68° C. for 80 seconds was carried out 35 times.

3. Restriction Enzyme Treatment

Twenty-five microliters of each of TE saturated phenol and CIA (a mixture of chloroform and isoamyl alcohol at a ratio of 24:1) was added to the reaction liquid after PCR, and the mixture was adequately shaken. Centrifugation was performed at 4° C. at 20000×g for 5 minutes. The supernatant was recovered in a new 1.5 mL tube, and 50 μL of CIA was added. Centrifugation was performed at 4° C. at 20000×g for 5 minutes. The supernatant was recovered in a new 1.5 mL tube, and 125 μL of ethanol and 5 μL of 2M NaCl were added. Centrifugation was performed at 4° C. at 20000×g for 20 minutes. The supernatant was discarded, and the pellet was air-dried. The pellet was dissolved by adding 10 μL of Milli-Q water. A restriction enzyme reaction liquid was prepared as in the table below, and reacted at 37° C. for 16 hours.

TABLE 4

| Sample name | DNA | 0.1% BSA | 10 × M Buffer | Xba I | Hind III | Pure water |
|---|---|---|---|---|---|---|
| PCR product | Pellet | 3 | 3 | 1 | 1 | 22 |
| pcDNA3.1 Hygro (−) | 1 | 3 | 3 | 1 | 1 | 21 |

Unit: μL
Xba I, Hind III: Toyobo
pcDNA3.1 Hygro (−): Thermo

4. Ligation

All the restriction enzyme reaction liquid was subjected to electrophoresis with 1% agarose gel. The major band was cut out and the DNA was purified with Gel Extraction kit. A mixture of 25 fmol of plasmid and 125 fmol of insert, and DNA Ligation kit mighty mix (Takara) with the same volume was reacted at 16° C. for 16 hours.

5. Transformation of *Escherichia coli*

The ligation product was added to 100 μL of DH5c competent cell (Nippon Gene), and placed on ice for 30 minutes. A heat shock was applied at 42° C. for 60 seconds. Three-hundred microliters of SOC medium was added, and the mixture was incubated at 37° C. for 1 hour. All the mixture was applied to LB (containing ampicillin at 100 μg/mL). Incubation was performed at 37° C. for 14 hours.

6. Miniprep

Two microliters of 100 mg/mL ampicillin was added to 2 mL of LB medium. Colonies were picked up with a toothpick, then placed in medium, and shaken at 37° C. for 16 hours. One milliliter of the bacterial solution was taken, and centrifuged at room temperature at 1000×g for 5 minutes. The supernatant was removed, and 100 μL of ice-cooled Sol I (50 mM sucrose, 25 mM Tris-HCl (pH 8.0) and 10 mM EDTA) was added and resuspended. Two-hundred microliters of Sol II (0.2M NaOH and 1% SDS) was added and mixed by inversion, and left standing on ice for 5 minutes. One-hundred and fifty microliters of ice-cooled Sol III (3M potassium acetate and 2M acetic acid) was added and mixed by inversion. Centrifugation was performed at 12000×g at 4° C. for 5 minutes. The supernatant was recovered, and 1 μL of RNase A (Sigma Aldrich) at 10 mg/mL was added, and the mixture was incubated at 37° C. for 1 hour. Each 255 μL of TE saturated phenol and CIA was added, and the mixture was adequately shaken. Centrifugation was performed at 4° C. at 12000×g for 5 minutes. The supernatant was recovered, 450 μL of CIA was added, and the mixture was adequately shaken. Centrifugation was performed at 4° C. at 12000×g for 5 minutes. The supernatant was recovered, 450 μL of 2-propanol was added, and the mixture was adequately stirred. Centrifugation was performed at 4° C. at 18000×g for 20 minutes. The supernatant was removed, and 1 mL of 75% ethanol was added. Centrifugation was performed at 18000×g at 4° C. for 5 minutes. The supernatant was removed, and the pellet was air-dried. The pellet was dissolved in 10 μL of TE buffer (pH 8.0). A mixture of 1 μL of each DNA solution, 2 μL of 10×M buffer, 2 μL of 0.1% BSA, 14 μL of Milli-Q water, 0.5 μL of Xba I and 0.5 μL of Hind III was incubated at 37° C. for 1 hour. Four microliters of 6×DNA sample buffer was added, and the mixture was subjected to electrophoresis with 1% agarose gel.

7. Midiprep

Colonies having a plasmid in which the insert had been accurately inserted in the miniprep were put in 1 mL of LB medium (containing ampicillin at 100 μg/mL), and cultured for 12 hours at 37° C. The cells were transferred to 200 mL of LB medium (containing ampicillin at 100 μg/mL), and cultured at 37° C. for 16 hours. DNA was extracted and purified using Hipure plasmid midiprep kit (Thermo). The sequence was checked to determine whether the obtained plasmid contained an intended mutation (NEU1 variant-introduced plasmid, FIG. 1).

8. Transfection into HEK293 Cell

DMEM (glucose at 4500 mg/mL) (Sigma Aldrich) with fetal bovine serum (Biosera) at final concentration of 10%, and PBS were warmed. The medium for HEK293 cultured in a 10 cm dish (Iwaki Collagen type I coated) was suctioned with an aspirator, and washed with 4 mL of 1×PBS. One milliliter of 0.05% trypsin-1 mM EDTA/PBS was added, and the cells were cultured at 37° C. for 2 minutes. One milliliter of DMEM was added, and cells were peeled off, and fully recovered in a 15 mL tube. The cells were centrifuged at 200×g at room temperature for 5 minutes, the supernatant was removed, the cells were suspended in 1 mL of DMEM, and 30 μL of the suspension was recovered and added to 1.5 mL tube. The cells were stained by adding and mixing 30 μL of 0.3% trypan blue. The cells were counted using a blood cell counting plate. The cells at 1×10⁶ were seeded on 35 mm dish (Iwaki Collagen type I coated). DMEM was added to a final concentration of 1.5 mL. The cells were cultured at 5% $CO_2$ and 37° C. for 24 hours. Opti-MEM (Thermo) was dispensed by 150 μL×2× number of plasmids. To one side, 2.5 μg of each plasmid and 5 μL of P3000 (Thermo) were added. To the other side, 7.5 μL of Lipofectamine 3000 (Thermo) was added. Both liquids were mixed and placed at room temperature for 15 minutes. The mixed liquid was applied to the cells, and the cells were cultured for 24 hours. The medium was replaced by 2 mL of new DMEM.

9. Confirmation of NEU1 Activity

The neuraminidase activity of each of wild-type NEU1 and NEU1 variants 1 and 2 was measured in accordance with the method described in the above <Measurement of neuraminidase activity>. A value obtained by subtracting the measured value of neuraminidase activity of NEU1-non-introduced cell from the obtained measured value was defined as neuraminidase activity. The results are shown in the table below and in FIG. 2. Both variants 1 and 2 had relatively high activity although they had activity lower than that of wild-type NEU1.

TABLE 5

|  | Wild type | Variant 1 | Variant 2 |
| --- | --- | --- | --- |
| Activity (nmol/hr/mg protein) | 146 | 114 | 69 |

Example 2. Confirmation of Whether Modified Neuraminidase is Crystallized or not 1. Transfection into CHO Cell CHO cells were transfected with a plasmid containing a gene encoding the wild-type NEU1 and NEU1 variant 1 (hereinafter, NEU1 variant 1 is also referred to simply as a NEU1 variant unless otherwise specified). Specifically, the transfection was performed in accordance with the following procedure. F-10 Ham (Sigma Aldrich) with fetal bovine serum (Biosera) at final concentration of 10%, and PBS were warmed. The medium for CHO cultured in 10 cm dish (Greiner) was suctioned with an aspirator, and washed with 5 mL of 1×PBS. One milliliter of 0.05% trypsin-1 mM EDTA/PBS was added, and the cells were cultured at 37° C. for 2 minutes. One milliliter of F-10 Ham was added, and cells were peeled off, and fully recovered in a 15 mL tube. The cells were centrifuged at 200×g at room temperature for 5 minutes, the supernatant was removed, the cells were suspended in 1 mL of F-10 Ham, and 30 μL of the suspension was recovered, and added to 1.5 mL tube. The cells were stained by adding and mixing 30 μL of 0.3% trypan blue. The cells were counted using a blood cell counting plate. The cells at 1×10⁶ were seeded on 35 mm dish (Greiner). F-10 Ham was added to a final concentration of 1.5 mL. The cells were cultured at 5% $CO_2$ and 37° C. for 24 hours. Opti-MEM (Thermo) was dispensed by 150 μL×2×number of plasmids. To one side, 2.5 μg of each plasmid and 5 μL of P3000 (Thermo) were added. To the other side, 7.5 μL of Lipofectamine 3000 (Thermo) was added. Both the liquids were mixed and placed at room temperature for 15 minutes. The mixed liquid was applied to the cells, and the cells were cultured for 24 hours. The medium was replaced by 2 mL of new F-10 Ham.

2. Observation of Intracellular Crystallization

In accordance with the method described in the above <Immunofluorescence staining>, immunostaining was performed using anti-NEU1 antibody for NEU1 and anti-LAMP1 for lysosomes four days after introduction of genes.

The results for the wild type are shown in FIG. 3, and the results for variant 1 are shown in FIG. 4. As shown in FIG. 3, crystallization of NEU1 was observed in the wild type. As shown in FIG. 4, crystallization of NEU1 was not observed in variant 1. For variant 2, slight crystallization was observed, which was much smaller as compared to the wild type. As shown in the figure, NEU1 was little co-localized with lysosomes.

Example 3. Co-Localization of NEU1 with Lysosome in Cathepsin A-Overexpressing Cell Transformation was performed in accordance with a known method to prepare a pCXN$_2$ plasmid having the full length of human cathepsin A (CTSA) cDNA (SEQ ID NO: 14) (referred to as pCXN$_2$ CTSA) (FIG. 5). CHO cells were transfected with pCXN$_2$ CTSA in accordance with the method described above. After 24 hours from replacement of the medium, the medium was replaced by 2 mL of new medium. G418 (Invivogen) at 400 μg/mL was added as a selecting drug, and the cells were cultured for 3 days. The medium was replaced, the selecting drug was added again, and the cells were cultured for further 1 week. The medium was replaced by medium free of the selecting drug to increase the number of cells. The NEU1 variant 1 was introduced into the obtained CTSA overexpression cells in accordance with the above-described method, and immunostaining was performed. The results are shown in FIG. 6. As shown in the figure, the NEU1 variant was co-localized with a lysosome in CTSA overexpression cells. This indicates that NEU1 is transported to a lysosome if sufficient CTSA is present.

Example 4. Preparation of Vector that Coexpresses Two Genes (CTSA and NEU1 Variant)

1. cDNA Amplification of NEU1 Variant 1 (Mod NEU1) and Incorporation into Vector The vector was prepared in accordance with the same procedure as in Example 1.1 above using following primers:

forward primer: TTTTGAATTCCACCATGACTGGG-GAGCGACC (SEQ ID NO: 15); and reverse primer: AAAAAGATCTTCAGAGTGTCC-CATAGACAC (SEQ ID NO: 16).

2. Restriction Enzyme Treatment

Treatment was carried out in the same procedure as in Example 1.3 except that the restriction enzyme reaction liquid was prepared as shown in the table below.

TABLE 6

| Sample name | DNA | 10 × M Buffer | EcoR I | Bgl II | Pure water |
|---|---|---|---|---|---|
| PCR product | Pellet | 3 | 1 | 1 | 25 |
| pBI-CMV1 | 1 | 3 | 1 | 1 | 24 |

Unit: μL
EcoR I: NEB
Bgl II: Toyobo
pBI-CMV1: Takara

3. Ligation, 4. Transformation of *Escherichia coli* and 5. Miniprep

Treatment was carried out in the same procedure as in Examples 1.4 to 6 except that 0.5 μL of EcoR I and 0.5 μL of Bgl II were used as restriction enzymes. The plasmid in which the obtained insert was accurately incorporated was defined as pBI-CMV1 mod NEU1 and used for the next incorporation of CTSA cDNA.

6. CTSA cDNA Amplification

A gene encoding CTSA cDNA (SEQ ID NO: 14) was treated in accordance with the same procedure as in Example 1.1 using the following primers:

forward primer: TTTTAGATCTCACCAT-GATCCGAGCCGCGCC (SEQ ID NO: 17); and reverse primer: AAAAGCGGCCGCTCAGTATGGCTGCTTGTTC (SEQ ID NO: 18), and pCXN$_2$ CTSA as a template plasmid.

7. Restriction Enzyme Treatment

Treatment was carried out in the same procedure as in Example 1.3 except that the restriction enzyme reaction liquid was prepared as shown in the table below.

TABLE 7

| Sample name | DNA | 0.1% BSA | 10 × M Buffer | Bgl II | Not I | Pure water |
|---|---|---|---|---|---|---|
| PCR product | Pellet | 3 | 3 | 1 | 1 | 22 |
| pBI-CMV1 mod NEU1 | 1 | 3 | 3 | 1 | 1 | 21 |

Unit: μL
Not I: NEB

8. Ligation, 9. Transformation of *Escherichia coli* and 10. Miniprep

Treatment was carried out in the same procedure as in Examples 1.4 to 6 except that 0.5 μL of Bgl II and 0.5 μL of Not I were used as restriction enzymes. The plasmid in which the obtained insert was accurately incorporated was defined as pBI-CMV1 CTSA+mod NEU1 (FIG. 7) and used for subsequent experiments.

11. Midiprep

Treatment was carried out in the same manner as in Example 1.7.

Example 5. Enzyme Activity in Cells into which Plasmids are Introduced

In addition to the above CTSA+mod NEU1, the plasmids of EGFP (negative control, FIG. 8), CTSA (FIG. 5) and mod NEU1 (FIG. 1) were each introduced to CTSA knockout (KO) or NEU1 knockout HEK293 cells in accordance with the above-described method. After introduction, cells were lysed with a surfactant, and neuraminidase activity and carboxypeptidase activity were measured in accordance with the above-described method. The results are shown in FIGS. 9 to 12. For cells into which a plasmid expressing both enzymes was introduced simultaneously, neuramini-dase activity and carboxypeptidase activity increased in both CTSA KO and NEU1 KO cells. In addition, for cells into which a plasmid expressing only neuraminidase was introduced, neuraminidase activity equivalent to that in normal HEK293 was exhibited in NEU1 KO cells, whereas neuraminidase activity lower than that in normal HEK293 cells was exhibited in CTSA KO cells. This revealed that CTSA activity was important for neuraminidase activity. Even a plasmid into which only mod NEU1 was introduced exhibited almost an ordinary level of NEU1 activity. Thus, the variant is considered to be more effective than wild-type NEU1 when considering that crystallization does not occur. In addition, it is shown that a vector that coexpresses CTSA and NEU1 will be effective for gene therapy of lysosomal storage diseases, particularly galactosialidosis and sialido-sis.

Example 6. Preparation of CTSA+Mod NEU1-Coexpressing AAV2

1. Preparation of pBI-CMV1 CTSA+Mod NEU1 NV for Template

Treatment was carried out in the same procedure as in Examples 1.3 to 6 except that the restriction enzyme reaction liquid was prepared as the table below, the amount of Milli-Q water used for dissolving the air-dried pellet was changed from 10 μL to 8 μL, and 0.5 μL of EcoR V and 0.5 μL of Xho I (Takara) were used as restriction enzymes. A vector with one band was defined as pBI-CMV1 CTSA+mod NEU1 NV, and used as a template for preparation of a vector for production of AAV (FIG. 13).

TABLE 8

| Sample name | DNA | 0.1% BSA | 10 × M Buffer | EcoR V | Not I | Pure water |
|---|---|---|---|---|---|---|
| pBI-CMV1 CTSA + Ng3 NEU1 | 1 | 3 | 3 | 1 | 1 | 21 |

Unit: μL

Not I: NEB

2. CTSA, Mod NEU1 Coexpression Unit and EGFP cDNA AMPLIFICATION

Treatment was carried out in the same procedure as in Example 1.1 using the following primers:

forward primer: TTTTAAGCTTGAGTCAGT-GAGCGAGGAAGC (SEQ ID NO: 19), and

TTTTGAATTCCACCATGGTGAGCAAGGG (SEQ ID NO: 20); and reverse primer: TTTTTCTAGATCAGAGTGTCCCATA-GACACTG (SEQ ID NO: 21), and AAAAAGATCTTTACTTGTACAGCTCGTCCATGC (SEQ ID NO: 22), pBI-CMV1 CTSA+mod NEU1 NV as a template plasmid, and pEGFP-N1 (Takara).

3. Restriction Enzyme Treatment

Treatment was carried out in the same procedure as in Example 1.3 except that the restriction enzyme reaction liquid was prepared as shown in the table below.

TABLE 9

| Sample name | DNA | 0.1% BSA | 10 × M Buffer | Hind III | Xba I | Pure water |
|---|---|---|---|---|---|---|
| PCR product (CTSA + mod NEU1) | Pellet | 3 | 3 | 1 | 1 | 22 |
| pAAV-CMV | 1 | 3 | 3 | 1 | 1 | 21 |

Unit: μL

TABLE 10

| Sample name | DNA | 0.1% BSA | 10 × M Buffer | Bgl II | EcoR I | Pure water |
|---|---|---|---|---|---|---|
| PCR product (EGFP) | Pellet | 3 | 3 | 1 | 1 | 22 |
| pAAV-CMV | 1 | 3 | 3 | 1 | 1 | 21 |

Unit: μL

4. Ligation, 5. Transformation of *Escherichia coli* and 6. Miniprep

Treatment was carried out in the same procedure as in Examples 1.4 to 6 except that 0.5 μL of BgI II and 0.5 μL of Not I were used as restriction enzymes. The vector in which the obtained insert was accurately incorporated was defined as pAAV-CMV CTSA+mod NEU1 (FIG. 14) or pAAV-CMV EGFP, and used for subsequent experiments.

7. Midiprep

Treatment was carried out in the same manner as in Example 1.7.

Example 7. Transfection of CTSA+Mod NEU1-Coexpressing AAV2 into HEK293 Cell

1. Seeding of HEK293FT

DMEM (glucose at 4500 mg/mL) (Sigma Aldrich) with fetal bovine serum (Biosera) at final concentration of 10%, and PBS were warmed. The medium for HEK293 cultured in 10 cm dish (Iwaki Collagen type I coated) was suctioned with an aspirator, and washed with 4 mL of 1×PBS. One milliliter of 0.05% trypsin-1 mM EDTA/PBS was added, and the cells were cultured at 37° C. for 2 minutes. One milliliter of DMEM was added, and cells were peeled off, and fully collected in a 15 mL tube. The cells were centri-fuged at 200×g at room temperature for 5 minutes, the supernatant was removed, the cells were suspended in 3 mL of DMEM, and 30 μL of the suspension was recovered, and added to 1.5 mL tube. The cells were stained by adding and mixing 30 μL of 0.3% trypan blue. The cells were counted using a blood cell counting plate. The cells at $4 \times 10^6$ were seeded on 10 cm dish (Greiner). DMEM was added to a final concentration of 10 mL. The cells were cultured at 5% $CO_2$ and 37° C. for 24 hours.

2. Transfection

CalPhos Transfection Reagent (Takara) was used. Cal-cium Solution was diluted by 6 times with sterile water. To 1000 μL of diluted calcium solution, 6 μL of each of 3 types of plasmids (pAAV-CMV EGFP or pAAV CTSA+mod NEU1; pRC2-mi342; and pHelper, at a concentration of 1 μg/μL in each TE buffer (pH 8.0), FIG. 15) was added. One-thousand and eighteen microliters of 2×HBS was added, and the mixture was vigorously shaken 15 times to be mixed. The mixture was left standing at room temperature for 3 minutes, and fully added to the cells. After 12 hours, all the medium was replaced by 8 mL of DMEM (2% fetal bovine serum).

3. Extraction of AAV

One-hundred microliters of 0.5M EDTA-NaOH (pH 8.0) was added to the cells, and the cells were left standing at room temperature for 10 minutes. The cells were peeled off, and recovered in 15 mL tube. The dish was washed with 2 mL of DMEM+25 μL of 0.5M EDAT-NaOH (pH 8.0), and collected in the above-described tube. Centrifugation was performed at 1700×g at 4° C. for 10 minutes. The supernatant was removed as much as possible, and the cells were loosened by a vortex. Five-hundred microliters of AAV Extraction Solution A (Takara) was added. Vortex was performed for 15 seconds. The contents were transferred to 1.5 mL tube and centrifuged at 10000×g at 4° C. for 10 minutes. Vortex and centrifugation were performed again for 15 seconds. The supernatant was transferred to new 1.5 mL tube, 50 μL of AAV Extraction Solution B (Takara) was added, and the mixture was stirred. One-hundred microliters of the mixture was dispensed and stored at −80° C.

4. AAV Quantification

A DNase reaction solution was prepared by gently mixing 5 μL of an AAV solution, 12 μL of water, 2 μL of a 10× DNase buffer and 1 μL of DNase I (Takara) with pipetting, and the solution was reacted under conditions of 7° C. and 30 minutes to 95° C. and 10 minutes. The following primers:

forward primer: 5'-GGAACCCCTAGTGATGGAGTT (SEQ ID NO: 23); and reverse primer: 5'-CGGCCTCAGTGAGCGA (SEQ ID NO: 24) were used, and 10 μL of IQ CYBR Green supermix (2×) (Bio-Rad), 0.1 μL of a 100 μM forward primer, 0.1 μL of a 100 μM reverse primer and 4.8 μL of nuclease free water were mixed to prepare a master mix in a total amount of 15 μL/sample. pAAV-CMV was diluted to $2×10^9$ moles/μL.

The plasmid was diluted in stages as shown in the table below.

TABLE 11

| $2 × 10^9$ stock, or volume after dilution (μL) | Water volume | Molecule/μL |
|---|---|---|
| 10 | 90 | $2 × 10^8$ |
| 10 at $2 × 10^8$ dilution | 90 | $2 × 10^7$ |
| 10 at $2 × 10^7$ dilution | 90 | $2 × 10^6$ |
| 10 at $2 × 10^6$ dilution | 90 | $2 × 10^5$ |
| 10 at $2 × 10^5$ dilution | 90 | $2 × 10^4$ |

The sample was diluted as follows.

1:20 dilution: 5 μL of sample+95 μL of water,

1:100 dilution: 20 μL of 1:20 dilution sample+80 μL of water,

1:500 dilution: 20 μL of 1:100 dilution sample+80 μL of water, and

1:2500 dilution: 20 μL of 1:500 dilution sample+80 μL of water

5 μL of each of the samples and the standard was applied to each well of 96-well plate, 15 μL of master mix was added to each thereof, and mixing was performed by pipetting. PCR was carried out under the conditions of 95° C. and 3 minutes/95° C. and 15 seconds/60° C. and 60 seconds/reading plate/40 cycles from step 3/melting curve at 55° C. to 95° C. A Bio-Rad CFX Connect real-time PCR analysis system was used for analysis.

5. Measurement of Neuraminidase Activity and Carboxypeptidase Activity

A virus-containing extract was added to NEU1 knockout (KO) or CTSA KO HEK293 at $1×10^5$ vg/cell, and the mixture was cultured for 1 week. Cells were lysed with a surfactant, neuraminidase activity was measured with 4-MU-NANA, and carboxypeptidase activity was measured with Z-Phe-Leu-OH. The results are shown in FIGS. 16 and 17. As shown in the figure, addition of AAV2 CTSA+mod NEU1 increased neuraminidase activity and carboxypeptidase activity in both CTSA KO and NEU1 KO HEK293.

Example 7. Infection of CTSA+Mod NEU1 Coexpression AAV2

A virus-containing extract was added to galactosialidosis (GS) or sialidosis (SD) patient-derived skin fibroblasts at $2×10^5$ vg/cell or $1×10^5$ vg/cell, and culturing was performed for 1 week. Galactosialidosis patient-derived skin fibroblasts F598, sialidosis patient-derived skin fibroblasts F643, and healthy person-derived skin fibroblasts F258 as a positive control were used. The cells were lysed with a surfactant, and neuraminidase activity was measured with 4-MU-NANA. The results are shown in FIGS. 18 and 19. Addition of AAV2 CTSA+mod NEU1 increased neuraminidase activity in both GS patient-derived and SD patient-derived skin fibroblasts.

Example 8. NEU1 Variant is Secreted into CHO Cell Supernatant

CHO cells transfected in the same procedure as in Example 2.1 were cultured in a serum-free medium, the culture supernatant was collected, purified CTSA was added, and neuraminidase activity was measured in accordance with the above-described method. The results are shown in FIG. 20. As a result, 1.18 mg of NEU1 modification type 1 was secreted per liter of medium.

Example 9. Purification of CTSA+Mod NEU1 Coexpression AAV2 Vector

A vector is purified in accordance with the discontinuous gradient method described in Zolotukhin et. Al. Gene Ther., 6, 973-985 (1999). PBS containing 1 mM magnesium chloride (PBS-MK) is added to the cryopreserved cells to thaw the cells. DNase I and RNase A are added, and the mixture is reacted at 37° C. for 1 hour. Centrifugation is performed at 10000×g at 10° C. for 5 minutes, and the supernatant is filtrated with a 0.45 μm filter. PBS-MK is made to pass through the filter, and the liquid remaining in the filter is forced out. The sample is added to an ultracentrifugation tube, and 15% iodixanol/1MNaCl/PBS-MK is applied under the sample with a syringe with a long needle. Subsequently, 25% iodixanol/phenol red/PBS-MK is applied to the lower layer. In addition, 40% iodixanol/PBS-MK is applied to the lower layer. Further, 54% iodixanol/PBS-MK is applied to the lower layer. Centrifugation is performed at 18° C. for 2 hours at 50000 rpm (rotor used is 70.1 Ti, 200000×g). After the centrifugation, the 40% iodixanol layer is collected. The buffer is replaced by PBS with 100 kDa cut Amicon Ultra.

Example 10. In Vivo Intracerebroventricular Administration Protocol

A CTSA mutant mouse is anesthetized, and its scalp is cut open. A two-step needle is inserted at a position of 1 mm from to the right of the bregma to the right and 0.5 mm to the tail, and 25 μL of an AAV solution is administered. The mouse is placed on a body warmer to maintain the body temperature until the mouse awakes from anesthesia. After one week, the mouse is dissected to isolate the cerebrum and the cerebellum separately, and enzyme activity is measured.

The invention claimed is:

1. A modified neuraminidase comprising an amino acid sequence having a sequence identity of at least 90% to the amino acid sequence set forth in SEQ ID NO: 1, wherein the amino acid sequence has the following mutations with respect to the amino acid sequence set forth in SEQ ID NO: 1:

(i) W173N and K175S mutations; or
(ii) K358N mutation.

2. The modified neuraminidase according to claim 1, wherein the modified neuraminidase comprises the sequence set forth in SEQ ID NO: 2 or SEQ ID NO: 3.

3. A nucleic acid encoding the modified neuraminidase according to claim 1.

4. A vector comprising the nucleic acid according to claim 3.

5. The vector according to claim 4, wherein the vector is an AAV vector.

6. The vector according to claim 4, the vector further comprising a nucleic acid encoding cathepsin A.

7. A pharmaceutical composition comprising the modified neuraminidase according to claim 1.

8. The pharmaceutical composition according to claim 7, for treatment of a disease associated with deletion or attenuation of neuraminidase 1 activity.

9. A nucleic acid encoding the modified neuraminidase according to claim 2.

10. A vector comprising the nucleic acid according to claim 9.

11. The vector according to claim 10, wherein the vector is an AAV vector.

12. The vector according to claim 5, further comprising a nucleic acid encoding cathepsin A.

13. The vector according to claim 10, further comprising a nucleic acid encoding cathepsin A.

14. The vector according to claim 11, further comprising a nucleic acid encoding cathepsin A.

15. A pharmaceutical composition comprising the modified neuraminidase according to claim 2.

16. A pharmaceutical composition comprising the vector according to claim 4.

17. A pharmaceutical composition comprising the vector according to claim 5.

18. A pharmaceutical composition comprising the vector according to claim 6.

19. A pharmaceutical composition comprising the vector according to claim 10.

20. A pharmaceutical composition comprising the vector according to claim 14.

\* \* \* \* \*

SEQUENCE LISTING

<160> NUMBER OF SEQ ID NOS: 24

<210> SEQ ID NO 1
<211> LENGTH: 415
<212> TYPE: PRT
<213> ORGANISM: Homo sapiens

<400> SEQUENCE: 1

```
Met Thr Gly Glu Arg Pro Ser Thr Ala Leu Pro Asp Arg Arg Trp Gly
1               5                   10                  15

Pro Arg Ile Leu Gly Phe Trp Gly Gly Cys Arg Val Trp Val Phe Ala
            20                  25                  30

Ala Ile Phe Leu Leu Leu Ser Leu Ala Ala Ser Trp Ser Lys Ala Glu
            35                  40                  45

Asn Asp Phe Gly Leu Val Gln Pro Leu Val Thr Met Glu Gln Leu Leu
        50                  55                  60

Trp Val Ser Gly Arg Gln Ile Gly Ser Val Asp Thr Phe Arg Ile Pro
65                  70                  75                  80

Leu Ile Thr Ala Thr Pro Arg Gly Thr Leu Leu Ala Phe Ala Glu Ala
                85                  90                  95

Arg Lys Met Ser Ser Ser Asp Glu Gly Ala Lys Phe Ile Ala Leu Arg
            100                 105                 110

Arg Ser Met Asp Gln Gly Ser Thr Trp Ser Pro Thr Ala Phe Ile Val
            115                 120                 125

Asn Asp Gly Asp Val Pro Asp Gly Leu Asn Leu Gly Ala Val Val Ser
        130                 135                 140

Asp Val Glu Thr Gly Val Val Phe Leu Phe Tyr Ser Leu Cys Ala His
145                 150                 155                 160

Lys Ala Gly Cys Gln Val Ala Ser Thr Met Leu Val Trp Ser Lys Asp
                165                 170                 175

Asp Gly Val Ser Trp Ser Thr Pro Arg Asn Leu Ser Leu Asp Ile Gly
            180                 185                 190

Thr Glu Val Phe Ala Pro Gly Pro Gly Ser Gly Ile Gln Lys Gln Arg
            195                 200                 205

Glu Pro Arg Lys Gly Arg Leu Ile Val Cys Gly His Gly Thr Leu Glu
        210                 215                 220

Arg Asp Gly Val Phe Cys Leu Leu Ser Asp Asp His Gly Ala Ser Trp
225                 230                 235                 240

Arg Tyr Gly Ser Gly Val Ser Gly Ile Pro Tyr Gly Gln Pro Lys Gln
                245                 250                 255

Glu Asn Asp Phe Asn Pro Asp Glu Cys Gln Pro Tyr Glu Leu Pro Asp
            260                 265                 270

Gly Ser Val Val Ile Asn Ala Arg Asn Gln Asn Asn Tyr His Cys His
        275                 280                 285

Cys Arg Ile Val Leu Arg Ser Tyr Asp Ala Cys Asp Thr Leu Arg Pro
        290                 295                 300

Arg Asp Val Thr Phe Asp Pro Glu Leu Val Asp Pro Val Val Ala Ala
305                 310                 315                 320

Gly Ala Val Val Thr Ser Ser Gly Ile Val Phe Phe Ser Asn Pro Ala
                325                 330                 335

His Pro Glu Phe Arg Val Asn Leu Thr Leu Arg Trp Ser Phe Ser Asn
            340                 345                 350

Gly Thr Ser Trp Arg Lys Glu Thr Val Gln Leu Trp Pro Gly Pro Ser
            355                 360                 365
```

-continued

```
Gly Tyr Ser Ser Leu Ala Thr Leu Glu Gly Ser Met Asp Gly Glu Glu
    370             375             380

Gln Ala Pro Gln Leu Tyr Val Leu Tyr Glu Lys Gly Arg Asn His Tyr
385             390             395             400

Thr Glu Ser Ile Ser Val Ala Lys Ile Ser Val Tyr Gly Thr Leu
            405             410             415

<210> SEQ ID NO 2
<211> LENGTH: 415
<212> TYPE: PRT
<213> ORGANISM: Artificial Sequence
<220> FEATURE:
<223> OTHER INFORMATION: Modified neuraminidase

<400> SEQUENCE: 2

Met Thr Gly Glu Arg Pro Ser Thr Ala Leu Pro Asp Arg Arg Trp Gly
1               5               10              15

Pro Arg Ile Leu Gly Phe Trp Gly Gly Cys Arg Val Trp Val Phe Ala
            20              25              30

Ala Ile Phe Leu Leu Leu Ser Leu Ala Ala Ser Trp Ser Lys Ala Glu
            35              40              45

Asn Asp Phe Gly Leu Val Gln Pro Leu Val Thr Met Glu Gln Leu Leu
    50              55              60

Trp Val Ser Gly Arg Gln Ile Gly Ser Val Asp Thr Phe Arg Ile Pro
65              70              75              80

Leu Ile Thr Ala Thr Pro Arg Gly Thr Leu Leu Ala Phe Ala Glu Ala
            85              90              95

Arg Lys Met Ser Ser Ser Asp Glu Gly Ala Lys Phe Ile Ala Leu Arg
            100             105             110

Arg Ser Met Asp Gln Gly Ser Thr Trp Ser Pro Thr Ala Phe Ile Val
            115             120             125

Asn Asp Gly Asp Val Pro Asp Gly Leu Asn Leu Gly Ala Val Val Ser
    130             135             140

Asp Val Glu Thr Gly Val Val Phe Leu Phe Tyr Ser Leu Cys Ala His
145             150             155             160

Lys Ala Gly Cys Gln Val Ala Ser Thr Met Leu Val Asn Ser Ser Asp
            165             170             175

Asp Gly Val Ser Trp Ser Thr Pro Arg Asn Leu Ser Leu Asp Ile Gly
            180             185             190

Thr Glu Val Phe Ala Pro Gly Pro Gly Ser Gly Ile Gln Lys Gln Arg
            195             200             205

Glu Pro Arg Lys Gly Arg Leu Ile Val Cys Gly His Gly Thr Leu Glu
    210             215             220

Arg Asp Gly Val Phe Cys Leu Leu Ser Asp Asp His Gly Ala Ser Trp
225             230             235             240

Arg Tyr Gly Ser Gly Val Ser Gly Ile Pro Tyr Gly Gln Pro Lys Gln
            245             250             255

Glu Asn Asp Phe Asn Pro Asp Glu Cys Gln Pro Tyr Glu Leu Pro Asp
            260             265             270

Gly Ser Val Val Ile Asn Ala Arg Asn Gln Asn Asn Tyr His Cys His
            275             280             285

Cys Arg Ile Val Leu Arg Ser Tyr Asp Ala Cys Asp Thr Leu Arg Pro
    290             295             300

Arg Asp Val Thr Phe Asp Pro Glu Leu Val Asp Pro Val Val Ala Ala
305             310             315             320
```

-continued

```
Gly Ala Val Val Thr Ser Ser Gly Ile Val Phe Phe Ser Asn Pro Ala
            325                 330                 335

His Pro Glu Phe Arg Val Asn Leu Thr Leu Arg Trp Ser Phe Ser Asn
            340                 345                 350

Gly Thr Ser Trp Arg Lys Glu Thr Val Gln Leu Trp Pro Gly Pro Ser
            355                 360                 365

Gly Tyr Ser Ser Leu Ala Thr Leu Glu Gly Ser Met Asp Gly Glu Glu
        370                 375                 380

Gln Ala Pro Gln Leu Tyr Val Leu Tyr Glu Lys Gly Arg Asn His Tyr
385                 390                 395                 400

Thr Glu Ser Ile Ser Val Ala Lys Ile Ser Val Tyr Gly Thr Leu
                405                 410                 415
```

<210> SEQ ID NO 3
<211> LENGTH: 415
<212> TYPE: PRT
<213> ORGANISM: Artificial Sequence
<220> FEATURE:
<223> OTHER INFORMATION: Modified neuraminidase

<400> SEQUENCE: 3

```
Met Thr Gly Glu Arg Pro Ser Thr Ala Leu Pro Asp Arg Arg Trp Gly
1               5                   10                  15

Pro Arg Ile Leu Gly Phe Trp Gly Gly Cys Arg Val Trp Val Phe Ala
            20                  25                  30

Ala Ile Phe Leu Leu Leu Ser Leu Ala Ala Ser Trp Ser Lys Ala Glu
            35                  40                  45

Asn Asp Phe Gly Leu Val Gln Pro Leu Val Thr Met Glu Gln Leu Leu
        50                  55                  60

Trp Val Ser Gly Arg Gln Ile Gly Ser Val Asp Thr Phe Arg Ile Pro
65                  70                  75                  80

Leu Ile Thr Ala Thr Pro Arg Gly Thr Leu Leu Ala Phe Ala Glu Ala
                85                  90                  95

Arg Lys Met Ser Ser Ser Asp Glu Gly Ala Lys Phe Ile Ala Leu Arg
            100                 105                 110

Arg Ser Met Asp Gln Gly Ser Thr Trp Ser Pro Thr Ala Phe Ile Val
            115                 120                 125

Asn Asp Gly Asp Val Pro Asp Gly Leu Asn Leu Gly Ala Val Val Ser
        130                 135                 140

Asp Val Glu Thr Gly Val Val Phe Leu Phe Tyr Ser Leu Cys Ala His
145                 150                 155                 160

Lys Ala Gly Cys Gln Val Ala Ser Thr Met Leu Val Trp Ser Lys Asp
                165                 170                 175

Asp Gly Val Ser Trp Ser Thr Pro Arg Asn Leu Ser Leu Asp Ile Gly
            180                 185                 190

Thr Glu Val Phe Ala Pro Gly Pro Gly Ser Gly Ile Gln Lys Gln Arg
            195                 200                 205

Glu Pro Arg Lys Gly Arg Leu Ile Val Cys Gly His Gly Thr Leu Glu
        210                 215                 220

Arg Asp Gly Val Phe Cys Leu Leu Ser Asp Asp His Gly Ala Ser Trp
225                 230                 235                 240

Arg Tyr Gly Ser Gly Val Ser Gly Ile Pro Tyr Gly Gln Pro Lys Gln
                245                 250                 255

Glu Asn Asp Phe Asn Pro Asp Glu Cys Gln Pro Tyr Glu Leu Pro Asp
            260                 265                 270
```

```
Gly Ser Val Val Ile Asn Ala Arg Asn Gln Asn Asn Tyr His Cys His
        275             280             285

Cys Arg Ile Val Leu Arg Ser Tyr Asp Ala Cys Asp Thr Leu Arg Pro
        290             295             300

Arg Asp Val Thr Phe Asp Pro Glu Leu Val Asp Pro Val Val Ala Ala
305             310             315             320

Gly Ala Val Val Thr Ser Ser Gly Ile Val Phe Phe Ser Asn Pro Ala
            325             330             335

His Pro Glu Phe Arg Val Asn Leu Thr Leu Arg Trp Ser Phe Ser Asn
            340             345             350

Gly Thr Ser Trp Arg Asn Glu Thr Val Gln Leu Trp Pro Gly Pro Ser
        355             360             365

Gly Tyr Ser Ser Leu Ala Thr Leu Glu Gly Ser Met Asp Gly Glu Glu
        370             375             380

Gln Ala Pro Gln Leu Tyr Val Leu Tyr Glu Lys Gly Arg Asn His Tyr
385             390             395             400

Thr Glu Ser Ile Ser Val Ala Lys Ile Ser Val Tyr Gly Thr Leu
            405             410             415
```

```
<210> SEQ ID NO 4
<211> LENGTH: 1248
<212> TYPE: DNA
<213> ORGANISM: Homo sapiens

<400> SEQUENCE: 4
atgactgggg agcgacccag cacggcgctc ccggacagac gctgggggcc gcggattctg      60
ggcttctggg gaggctgtag ggtttgggtg tttgccgcga tcttcctgct gctgtctctg     120
gcagcctcct ggtccaaggc tgagaacgac ttcggtctgg tgcagccgct ggtgaccatg     180
gagcaactgc tgtgggtgag cgggagacag atcggctcag tggacacctt ccgcatcccg     240
ctcatcacag ccactccgcg gggcactctt ctcgcctttg ctgaggcgag gaaaatgtcc     300
tcatccgatg aggggggccaa gttcatcgcc ctgcggaggt ccatggacca gggcagcaca     360
tggtctccta cagcgttcat tgtcaatgat ggggatgtcc ccgatgggct gaaccttggg     420
gcagtagtga gcgatgttga cacaggagta gtatttcttt tctactccct ttgtgctcac     480
aaggccggct gccaggtggc ctctaccatg ttggtatgga gcaaggatga tggtgtttcc     540
tggagcacac cccggaatct ctccctggat attggcactg aagtgtttgc ccctggaccg     600
ggctctggta ttcagaaaca gcgggagcca cggaagggcc gcctcatcgt gtgtggccat     660
gggacgctgg agcgggacgg agtcttctgt ctcctcagcg atgatcatgg tgcctcctgg     720
cgctacggaa gtggggtcag cggcatcccc tacggtcagc ccaagcagga aaatgatttc     780
aatcctgatg aatgccagcc ctatgagctc ccagatggct cagtcgtcat caatgcccga     840
aaccagaaca actaccactg ccactgccga attgtcctcc gcagctatga tgcctgtgat     900
acactaaggc cccgtgatgt gaccttcgac cctgagctcg tggaccctgt ggtagctgca     960
ggagctgtag tcaccagctc cggcattgtc ttcttctcca acccagcaca tccagagttc    1020
cgagtgaacc tgaccctgcg catggagcttc agcaatggta cctcatggcg gaaagagaca    1080
gtccagctat ggccaggccc cagtggctat tcatccctgg caaccctgga gggcagcatg    1140
gatggagagg agcaggcccc ccagctctac gtcctgtatg agaaaggccg gaaccactac    1200
acagagagca tctccgtggc caaaatcagt gtctatggga cactctga              1248
```

```
<210> SEQ ID NO 5
```

```
<211> LENGTH: 1248
<212> TYPE: DNA
<213> ORGANISM: Artificial Sequence
<220> FEATURE:
<223> OTHER INFORMATION: Modified neuraminidase

<400> SEQUENCE: 5
atgactgggg agcgacccag cacggcgctc ccggacagac gctgggggcc gcggattctg        60
ggcttctggg gaggctgtag ggtttgggtg tttgccgcga tcttcctgct gctgtctctg       120
gcagcctcct ggtccaaggc tgagaacgac ttcggtctgg tgcagccgct ggtgaccatg       180
gagcaactgc tgtgggtgag cgggagacag atcggctcag tggacacctt ccgcatcccg       240
ctcatcacag ccactccgcg gggcactctt ctcgcctttg ctgaggcgag gaaaatgtcc       300
tcatccgatg agggggccaa gttcatcgcc ctgcggaggt ccatggacca gggcagcaca       360
tggtctccta cagcgttcat tgtcaatgat ggggatgtcc ccgatgggct gaaccttggg       420
gcagtagtga gcgatgttga gacaggagta gtatttcttt tctactccct ttgtgctcac       480
aaggccggct gccaggtggc ctctaccatg ttggtaaaca gcagcgatga tggtgtttcc       540
tggagcacac cccggaatct ctccctggat attggcactg aagtgtttgc ccctggaccg       600
ggctctggta ttcagaaaca gcgggagcca cggaagggcc gcctcatcgt gtgtggccat       660
gggacgctgg agcgggacgg agtcttctgt ctcctcagcg atgatcatgg tgcctcctgg       720
cgctacggaa gtggggtcag cggcatcccc tacggtcagc ccaagcagga aaatgatttc       780
aatcctgatg aatgccagcc ctatgagctc ccagatggct cagtcgtcat caatgcccga       840
aaccagaaca ctaccactg ccactgccga attgtcctcc gcagctatga tgcctgtgat       900
acactaaggc cccgtgatgt gaccttcgac cctgagctcg tggaccctgt ggtagctgca       960
ggagctgtag tcaccagctc cggcattgtc ttcttctcca acccagcaca tccagagttc      1020
cgagtgaacc tgaccctgcg atggagcttc agcaatggta cctcatggcg gaaagagaca      1080
gtccagctat ggccaggccc cagtggctat tcatccctgg caaccctgga gggcagcatg      1140
gatggagagg agcaggcccc ccagctctac gtcctgtatg agaaaggccg gaaccactac      1200
acagagagca tctccgtggc caaaatcagt gtctatggga cactctga                   1248

<210> SEQ ID NO 6
<211> LENGTH: 1248
<212> TYPE: DNA
<213> ORGANISM: Artificial Sequence
<220> FEATURE:
<223> OTHER INFORMATION: Modified neuraminidase

<400> SEQUENCE: 6
atgactgggg agcgacccag cacggcgctc ccggacagac gctgggggcc gcggattctg        60
ggcttctggg gaggctgtag ggtttgggtg tttgccgcga tcttcctgct gctgtctctg       120
gcagcctcct ggtccaaggc tgagaacgac ttcggtctgg tgcagccgct ggtgaccatg       180
gagcaactgc tgtgggtgag cgggagacag atcggctcag tggacacctt ccgcatcccg       240
ctcatcacag ccactccgcg gggcactctt ctcgcctttg ctgaggcgag gaaaatgtcc       300
tcatccgatg agggggccaa gttcatcgcc ctgcggaggt ccatggacca gggcagcaca       360
tggtctccta cagcgttcat tgtcaatgat ggggatgtcc ccgatgggct gaaccttggg       420
gcagtagtga gcgatgttga gacaggagta gtatttcttt tctactccct ttgtgctcac       480
aaggccggct gccaggtggc ctctaccatg ttggtatgga gcaggatga tggtgtttcc       540 tggagcacac cccggaatct ctccctggat attggcactg aagtgtttgc ccctggaccg       600
```

```
ggctctggta ttcagaaaca gcgggagcca cggaagggcc gcctcatcgt gtgtggccat     660
gggacgctgg agcgggacgg agtcttctgt ctcctcagcg atgatcatgg tgcctcctgg     720
cgctacggaa gtggggtcag cggcatcccc tacggtcagc ccaagcagga aaatgatttc     780
aatcctgatg aatgccagcc ctatgagctc ccagatggct cagtcgtcat caatgcccga     840
aaccagaaca actaccactg ccactgccga attgtcctcc gcagctatga tgcctgtgat     900
acactaaggc cccgtgatgt gaccttcgac cctgagctcg tggaccctgt ggtagctgca     960
ggagctgtag tcaccagctc cggcattgtc ttcttctcca acccagcaca tccagagttc    1020
cgagtgaacc tgaccctgcg atggagcttc agcaatggta cctcatggcg gaacgagaca    1080
gtccagctat ggccaggccc cagtggctat tcatccctgg caaccctgga gggcagcatg    1140
gatggagagg agcaggcccc ccagctctac gtcctgtatg agaaaggccg gaaccactac    1200
acagagagca tctccgtggc caaaatcagt gtctatggga cactctga                 1248

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
tttttctaga caccatgact ggggagcgac                                        30

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
atataagctt tcagagtgtc ccataga                                           27

<210> SEQ ID NO 9
<211> LENGTH: 37
<212> TYPE: DNA
<213> ORGANISM: Artificial Sequence
<220> FEATURE:
<223> OTHER INFORMATION: Primer

<400> SEQUENCE: 9
ctaccatgtt ggtaaacagc agcgatgatg gtgtttc                                37

<210> SEQ ID NO 10
<211> LENGTH: 37
<212> TYPE: DNA
<213> ORGANISM: Artificial Sequence
<220> FEATURE:
<223> OTHER INFORMATION: Primer

<400> SEQUENCE: 10
gaaacaccat catcgctgct gtttaccaac atggtag                                37

<210> SEQ ID NO 11
<211> LENGTH: 23
<212> TYPE: DNA
<213> ORGANISM: Artificial Sequence
<220> FEATURE:
<223> OTHER INFORMATION: Primer
```

```
<400> SEQUENCE: 11
ctcatggcgg aacgagacag tcc                                              23

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ggactgtctc gttccgccat gag                                              23

<210> SEQ ID NO 13
<211> LENGTH: 480
<212> TYPE: PRT
<213> ORGANISM: Homo sapiens

<400> SEQUENCE: 13

Met Ile Arg Ala Ala Pro Pro Pro Leu Phe Leu Leu Leu Leu Leu Leu
1               5                   10                  15

Leu Leu Leu Val Ser Trp Ala Ser Arg Gly Glu Ala Ala Pro Asp Gln
            20                  25                  30

Asp Glu Ile Gln Arg Leu Pro Gly Leu Ala Lys Gln Pro Ser Phe Arg
        35                  40                  45

Gln Tyr Ser Gly Tyr Leu Lys Gly Ser Gly Ser Lys His Leu His Tyr
    50                  55                  60

Trp Phe Val Glu Ser Gln Lys Asp Pro Glu Asn Ser Pro Val Val Leu
65                  70                  75                  80

Trp Leu Asn Gly Gly Pro Gly Cys Ser Ser Leu Asp Gly Leu Leu Thr
                85                  90                  95

Glu His Gly Pro Phe Leu Val Gln Pro Asp Gly Val Thr Leu Glu Tyr
            100                 105                 110

Asn Pro Tyr Ser Trp Asn Leu Ile Ala Asn Val Leu Tyr Leu Glu Ser
        115                 120                 125

Pro Ala Gly Val Gly Phe Ser Tyr Ser Asp Asp Lys Phe Tyr Ala Thr
    130                 135                 140

Asn Asp Thr Glu Val Ala Gln Ser Asn Phe Glu Ala Leu Gln Asp Phe
145                 150                 155                 160

Phe Arg Leu Phe Pro Glu Tyr Lys Asn Asn Lys Leu Phe Leu Thr Gly
                165                 170                 175

Glu Ser Tyr Ala Gly Ile Tyr Ile Pro Thr Leu Ala Val Leu Val Met
            180                 185                 190

Gln Asp Pro Ser Met Asn Leu Gln Gly Leu Ala Val Gly Asn Gly Leu
        195                 200                 205

Ser Ser Tyr Glu Gln Asn Asp Asn Ser Leu Val Tyr Phe Ala Tyr Tyr
    210                 215                 220

His Gly Leu Leu Gly Asn Arg Leu Trp Ser Ser Leu Gln Thr His Cys
225                 230                 235                 240

Cys Ser Gln Asn Lys Cys Asn Phe Tyr Asp Asn Lys Asp Leu Glu Cys
                245                 250                 255

Val Thr Asn Leu Gln Glu Val Ala Arg Ile Val Gly Asn Ser Gly Leu
            260                 265                 270

Asn Ile Tyr Asn Leu Tyr Ala Pro Cys Ala Gly Gly Val Pro Ser His
        275                 280                 285

Phe Arg Tyr Glu Lys Asp Thr Val Val Val Gln Asp Leu Gly Asn Ile
```

```
         290                 295                 300

Phe Thr Arg Leu Pro Leu Lys Arg Met Trp His Gln Ala Leu Leu Arg
305                 310                 315                 320

Ser Gly Asp Lys Val Arg Met Asp Pro Pro Cys Thr Asn Thr Thr Ala
                325                 330                 335

Ala Ser Thr Tyr Leu Asn Asn Pro Tyr Val Arg Lys Ala Leu Asn Ile
                340                 345                 350

Pro Glu Gln Leu Pro Gln Trp Asp Met Cys Asn Phe Leu Val Asn Leu
            355                 360                 365

Gln Tyr Arg Arg Leu Tyr Arg Ser Met Asn Ser Gln Tyr Leu Lys Leu
        370                 375                 380

Leu Ser Ser Gln Lys Tyr Gln Ile Leu Leu Tyr Asn Gly Asp Val Asp
385                 390                 395                 400

Met Ala Cys Asn Phe Met Gly Asp Glu Trp Phe Val Asp Ser Leu Asn
                405                 410                 415

Gln Lys Met Glu Val Gln Arg Arg Pro Trp Leu Val Lys Tyr Gly Asp
            420                 425                 430

Ser Gly Glu Gln Ile Ala Gly Phe Val Lys Glu Phe Ser His Ile Ala
            435                 440                 445

Phe Leu Thr Ile Lys Gly Ala Gly His Met Val Pro Thr Asp Lys Pro
    450                 455                 460

Leu Ala Ala Phe Thr Met Phe Ser Arg Phe Leu Asn Lys Gln Pro Tyr
465                 470                 475                 480

<210> SEQ ID NO 14
<211> LENGTH: 1389
<212> TYPE: DNA
<213> ORGANISM: Homo sapiens

<400> SEQUENCE: 14
atgatccgag ccgcgccgcc gccgctgttc ctgctgctgc tgctgctgct gctgctagtg      60
tcctgggcgt cccgaggcga ggcagccccc gaccaggacg agatccagcg cctccccggg     120
ctggccaagc agccgtcttt ccgccagtac tccggctacc tcaaaggctc cggctccaag     180
cacctccact actggtttgt ggagtcccag aaggatcccg agaacagccc tgtggtgctt     240
tggctcaatg ggggtcccgg ctgcagctca ctagatgggc tcctcacaga gcatggcccc     300
ttcctgattg ccaatgtgtt atacctggag tccccagctg gggtgggctt ctcctactcc     360
gatgacaagt tttatgcaac taatgacact gaggtcgccc agagcaattt tgaggccctt     420
caagatttct tccgcctctt ccggagtac aagaacaaca aacttttcct gaccgggggag     480 agctatgctg gcatctacat ccccaccctg gccgtgctgg tcatgcagga tcccagcatg     540
aaccttcagg ggctggctgt gggcaatgga ctctcctcct atgagcagaa tgacaactcc     600
ctggtctact ttgcctacta ccatggcctt ctggggaaca ggctttggtc ttctctccag     660
acccactgct gctctcaaaa caagtgtaac ttctatgaca caaagacct ggaatgcgtg      720 accaatcttc aggaagtggc ccgcatcgtg ggcaactctg cctcaacat ctacaatctc      780 tatgccccgt gtctggagg ggtgcccagc cattttaggt atgagaagga cactgttgtg      840
gtccaggatt gggcaacat cttcactcgc ctgccactca gcggatgtg gcatcaggca      900 ctgctgcgct caggggataa agtgcgcatg dacccccct gcaccaacac aacagctgct      960
tccacctacc tcaacaaccc gtacgtgcgg aaggccctca catcccgga gcagctgcca     1020 caatgggaca tgtgcaactt ctggtaaac ttacagtacc gccgtctcta ccgaagcatg     1080
```

```
aactcccagt atctgaagct gcttagctca cagaaatacc agatcctatt atataatgga      1140
gatgtagaca tggcctgcaa tttcatgggg gatgagtggt ttgtggattc cctcaaccag      1200
aagatggagg tgcagcgccg gccctggtta gtgaagtacg gggacagcgg ggagcagatt      1260
gccggcttcg tgaaggagtt ctcccacatc gcctttctca cgatcaaggg cgccggccac      1320
atggttccca ccgacaagcc cctcgctgcc ttcaccatgt tctcccgctt cctgaacaag      1380
cagccatac                                                               1389
```

```
<210> SEQ ID NO 15
<211> LENGTH: 31
<212> TYPE: DNA
<213> ORGANISM: Artificial Sequence
<220> FEATURE:
<223> OTHER INFORMATION: Primer

<400> SEQUENCE: 15
ttttgaattc caccatgact ggggagcgac c                                       31
```

```
<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
aaaaagatct tcagagtgtc ccatagacac                                         30
```

```
<210> SEQ ID NO 17
<211> LENGTH: 31
<212> TYPE: DNA
<213> ORGANISM: Artificial Sequence
<220> FEATURE:
<223> OTHER INFORMATION: Primer

<400> SEQUENCE: 17
ttttagatct caccatgatc cgagccgcgc c                                       31
```

```
<210> SEQ ID NO 18
<211> LENGTH: 31
<212> TYPE: DNA
<213> ORGANISM: Artificial Sequence
<220> FEATURE:
<223> OTHER INFORMATION: Primer

<400> SEQUENCE: 18
aaaagcggcc gctcagtatg gctgcttgtt c                                       31
```

```
<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
ttttaagctt gagtcagtga gcgaggaagc                                         30
```

```
<210> SEQ ID NO 20
<211> LENGTH: 28
<212> TYPE: DNA
<213> ORGANISM: Artificial Sequence
<220> FEATURE:
<223> OTHER INFORMATION: Primer
```

-continued

```
<400> SEQUENCE: 20
ttttgaattc caccatggtg agcaaggg                              28

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
tttttctaga tcagagtgtc ccatagacac tg                         32

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
aaaaagatct ttacttgtac agctcgtcca tgc                        33

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23 ggaacccta gtgatggagt t                                      21

<210> SEQ ID NO 24
<211> LENGTH: 16
<212> TYPE: DNA
<213> ORGANISM: Artificial Sequence
<220> FEATURE:
<223> OTHER INFORMATION: Primer

<400> SEQUENCE: 24
cggcctcagt gagcga                                           16
```